United States Patent
Betts et al.

(10) Patent No.: US 12,263,324 B2
(45) Date of Patent: *Apr. 1, 2025

(54) VIAL SUPPORTER FOR MEDICAMENT PUMP

(71) Applicant: Tandem Diabetes Care, Inc., San Diego, CA (US)

(72) Inventors: Ryan William Betts, San Diego, CA (US); Maxwell Aaron Hume, San Diego, CA (US); Philip Sven Lamb, San Diego, CA (US); Michael Michaud, San Diego, CA (US); John Charles Nadworny, Poway, CA (US); William T. Trevaskis, San Marcos, CA (US); Steven Thuan Truong, San Diego, CA (US)

(73) Assignee: Tandem Diabetes Care, Inc., San Diego, CA (US)

(*) Notice: Subject to any disclaimer, the term of this patent is extended or adjusted under 35 U.S.C. 154(b) by 740 days.

This patent is subject to a terminal disclaimer.

(21) Appl. No.: 17/181,808

(22) Filed: Feb. 22, 2021

(65) Prior Publication Data

US 2021/0178054 A1     Jun. 17, 2021

Related U.S. Application Data

(63) Continuation of application No. 15/705,983, filed on Sep. 15, 2017, now Pat. No. 10,926,025.
(Continued)

(51) Int. Cl.
*A61M 5/142*   (2006.01)
*A61J 1/12*    (2006.01)
(Continued)

(52) U.S. Cl.
CPC ............ *A61M 5/142* (2013.01); *A61J 1/12* (2013.01); *A61J 1/14* (2013.01); *A61M 5/168* (2013.01);
(Continued)

(58) Field of Classification Search
CPC ......... A61J 1/2096; A61J 1/2089; A61J 1/20; A61J 1/2003; A61J 1/2093; A61J 1/12;
(Continued)

(56) References Cited

U.S. PATENT DOCUMENTS 2,077,240 A * 4/1937 Jeffords ............. A61M 5/1782
                                               206/229
2,627,857 A * 2/1953 Marcelli ............ A61M 5/1782
                                               141/330
(Continued)

FOREIGN PATENT DOCUMENTS

WO    2009013736    1/2009
WO    2009016636    2/2009
WO    2015115435    6/2015

*Primary Examiner* — Nathan R Price
*Assistant Examiner* — Mark A Igel
(74) *Attorney, Agent, or Firm* — Merchant & Gould P.C.

(57) ABSTRACT

Devices and methods for filling a medicament cartridge of a pump, including a user-wearable, ambulatory infusion pump. A device for supporting a medicament cartridge can comprise a body portion resembling a tray, with recesses disposed therein to support one or more of a cartridge body, cartridge tubing, interconnect fitting, and vial adapter. The recesses of the tray may be shaped to correspond to that component intended to be placed in its respective recess so to provide a visual indication to a user how to couple and align the various components necessary to fill the cartridge.

18 Claims, 24 Drawing Sheets

Related U.S. Application Data

(60) Provisional application No. 62/394,806, filed on Sep. 15, 2016.

(51) Int. Cl.
*A61J 1/14* (2023.01)
*A61M 5/168* (2006.01)
*B65B 3/00* (2006.01)
*F04B 43/10* (2006.01)

(52) U.S. Cl.
CPC ..... *B65B 3/003* (2013.01); *A61M 2205/3331* (2013.01); *F04B 43/10* (2013.01)

(58) Field of Classification Search
CPC .......... A61J 1/14; A61M 5/24; A61M 5/1413; A61M 5/1782; A61M 2209/045; A61M 2205/3331; A61M 5/142; A61M 5/168; B65B 3/003; F04B 43/10
See application file for complete search history.

(56) References Cited

U.S. PATENT DOCUMENTS

| | | | | |
|---|---|---|---|---|
| 3,245,194 A * | 4/1966 | Carski | ..................... | B65B 3/003 53/489 |
| 3,734,147 A * | 5/1973 | Borutta | .................. | B65B 3/003 141/378 |
| 3,833,030 A * | 9/1974 | Waldbauer, Jr. | .... | A61M 5/1782 141/26 |
| 3,853,158 A * | 12/1974 | Whitty | ................ | A61M 5/1782 141/330 |
| 3,875,979 A * | 4/1975 | Hults | ................... | A61M 5/1782 141/27 |
| 3,940,909 A * | 3/1976 | Cioni | ..................... | B65B 3/003 53/381.2 |
| 4,516,967 A * | 5/1985 | Kopfer | .................. | A61J 1/2096 604/87 |
| 4,883,101 A * | 11/1989 | Strong | ................ | A61M 5/1782 604/407 |
| 5,292,318 A * | 3/1994 | Haber | ................. | A61M 5/1782 604/407 |
| 5,334,162 A * | 8/1994 | Harris | .................. | A61J 1/2096 604/416 |
| 5,468,233 A * | 11/1995 | Schraga | ............. | A61M 5/1782 604/407 |
| 5,478,211 A * | 12/1995 | Dominiak | ........... | A61M 39/281 607/153 |
| 5,584,814 A * | 12/1996 | Schuster | ................ | B65B 3/003 222/326 |
| 5,743,312 A * | 4/1998 | Pfeifer | .................. | A61J 1/2089 604/416 |
| 5,827,262 A * | 10/1998 | Neftel | ................... | A61J 1/2096 604/82 |
| 5,858,001 A | 1/1999 | Tsals et al. | | |
| 5,894,870 A * | 4/1999 | Maxwell | ............... | A61J 1/2096 141/330 |
| 5,911,252 A * | 6/1999 | Cassel | .................... | B65B 3/003 604/407 |
| 6,006,798 A * | 12/1999 | Lindquist | ............ | A61M 5/1782 141/369 |
| 6,146,361 A | 11/2000 | Dibiasi et al. | | |
| 6,364,866 B1 * | 4/2002 | Furr | ..................... | A61M 5/1782 141/330 |
| 6,439,276 B1 * | 8/2002 | Wood | .................. | A61M 5/3205 141/97 |
| 6,648,859 B2 | 11/2003 | Bitdinger et al. | | |
| 6,649,403 B1 | 11/2003 | McDevitt et al. | | |
| 7,033,338 B2 | 4/2006 | Vilks et al. | | |
| 7,041,082 B2 | 5/2006 | Blomquist et al. | | |
| 7,195,616 B2 | 3/2007 | Diller et al. | | |
| 7,291,126 B2 | 11/2007 | Shekalim | | |
| 7,291,132 B2 | 11/2007 | Deruntz et al. | | |
| 7,311,693 B2 | 12/2007 | Shekalim | | |
| 7,316,899 B2 | 1/2008 | McDevitt et al. | | |
| 7,427,275 B2 | 9/2008 | Deruntz et al. | | |
| 7,442,186 B2 | 10/2008 | Blomquist | | |
| 7,510,544 B2 | 3/2009 | Vilks et al. | | |
| 7,651,868 B2 | 1/2010 | McDevitt et al. | | |
| 7,678,084 B2 | 3/2010 | Judson et al. | | |
| 7,695,454 B2 | 4/2010 | Barron et al. | | |
| 7,704,237 B2 | 4/2010 | Fisher et al. | | |
| 7,704,238 B2 | 4/2010 | Diller et al. | | |
| 7,736,344 B2 | 6/2010 | Moberg et al. | | |
| 7,744,589 B2 | 6/2010 | Mounce et al. | | |
| 7,857,791 B2 | 12/2010 | Jacobs et al. | | |
| 7,905,859 B2 | 3/2011 | Bynum et al. | | |
| 7,905,868 B2 | 3/2011 | Moberg et al. | | |
| 7,938,797 B2 | 5/2011 | Estes | | |
| 7,959,598 B2 | 6/2011 | Estes | | |
| 7,981,076 B2 | 7/2011 | Sullivan et al. | | |
| 8,021,334 B2 | 9/2011 | Shekalim | | |
| 8,221,385 B2 | 7/2012 | Estes | | |
| 8,234,126 B1 | 7/2012 | Estes | | |
| 8,277,435 B2 | 10/2012 | Estes | | |
| 8,287,487 B2 | 10/2012 | Estes | | |
| 8,287,495 B2 | 10/2012 | Michaud et al. | | |
| 8,360,114 B2 * | 1/2013 | Clark | ..................... | A61J 1/2096 141/330 |
| 8,573,027 B2 | 11/2013 | Rosinko et al. | | |
| 8,986,253 B2 | 3/2015 | DiPerna | | |
| 9,114,210 B2 | 8/2015 | Estes | | |
| 10,926,025 B2 * | 2/2021 | Betts | ...................... | A61M 5/142 |
| 2002/0049405 A1 * | 4/2002 | Deslauriers | ........... | B01F 35/181 604/82 |
| 2003/0100866 A1 * | 5/2003 | Reynolds | .................. | A61L 2/07 29/428 |
| 2003/0199847 A1 * | 10/2003 | Akerlund | .............. | A61J 1/2089 604/500 |
| 2003/0216683 A1 | 11/2003 | Shekalim | | |
| 2004/0069044 A1 * | 4/2004 | Lavi | ........................ | A61M 5/19 604/93.01 |
| 2005/0087256 A1 * | 4/2005 | Clark | ..................... | A61J 1/2096 141/97 |
| 2005/0092387 A1 | 5/2005 | Schorn et al. | | |
| 2006/0206054 A1 | 9/2006 | Shekalim | | |
| 2007/0088267 A1 | 4/2007 | Shekalim | | |
| 2007/0156092 A1 | 7/2007 | Estes et al. | | |
| 2007/0161955 A1 | 7/2007 | Bynum et al. | | |
| 2008/0051697 A1 | 2/2008 | Mounce et al. | | |
| 2008/0051698 A1 | 2/2008 | Mounce et al. | | |
| 2008/0051711 A1 | 2/2008 | Mounce et al. | | |
| 2008/0051727 A1 | 2/2008 | Moberg et al. | | |
| 2008/0215035 A1 | 9/2008 | Yodfat et al. | | |
| 2008/0306439 A1 * | 12/2008 | Nelson | ................... | A61J 1/2096 604/84 |
| 2009/0036870 A1 | 2/2009 | Mounce et al. | | |
| 2009/0270811 A1 | 10/2009 | Mounce et al. | | |
| 2009/0275887 A1 | 11/2009 | Estes | | |
| 2010/0049164 A1 | 2/2010 | Estes | | |
| 2010/0094251 A1 | 4/2010 | Estes | | |
| 2010/0174266 A1 | 7/2010 | Estes | | |
| 2010/0191182 A1 * | 7/2010 | Smith | .................... | A61J 1/2096 604/87 |
| 2010/0262078 A1 | 10/2010 | Blomquist | | |
| 2011/0004143 A1 * | 1/2011 | Beiriger | .............. | A61M 1/3622 604/6.11 |
| 2011/0004188 A1 | 1/2011 | Shekalim | | |
| 2011/0106045 A1 * | 5/2011 | Reynolds | ............... | A61J 1/2089 604/413 |
| 2011/0213329 A1 | 9/2011 | Yodfat et al. | | |
| 2012/0017688 A1 | 1/2012 | Shekalim | | |
| 2012/0160723 A1 * | 6/2012 | Harms | .................. | A61M 5/003 248/74.2 |
| 2012/0226238 A1 * | 9/2012 | Davies | ................ | A61M 5/3294 604/93.01 |
| 2013/0041258 A1 * | 2/2013 | Patrick | .............. | A61M 5/16827 600/439 |
| 2013/0053816 A1 | 2/2013 | DiPerna et al. | | |
| 2013/0324928 A1 | 12/2013 | Kruse | | |
| 2013/0331790 A1 | 12/2013 | Brown et al. | | |

(56) References Cited

U.S. PATENT DOCUMENTS

| | | |
|---|---|---|
| 2014/0276423 A1 | 9/2014 | Lecanu-Fayet |
| 2014/0378898 A1 | 12/2014 | Rosinko |
| 2015/0029816 A1* | 1/2015 | Beyer ................ B01F 35/7176 366/167.1 |
| 2015/0182693 A1 | 7/2015 | Rosinko |
| 2016/0339172 A1 | 11/2016 | Michaud et al. |
| 2017/0028132 A1* | 2/2017 | Cronenberg ........ A61M 5/2459 |
| 2017/0035962 A1 | 2/2017 | Lecanu-Fayet et al. |
| 2017/0049957 A1 | 2/2017 | Michaud |
| 2017/0112997 A1 | 4/2017 | Metzmaker et al. |
| 2017/0129763 A1* | 5/2017 | Fangrow, Jr. ......... A61J 1/2089 |
| 2017/0135903 A1* | 5/2017 | Wattelier ............. A61J 1/2068 |

* cited by examiner

VIAL SUPPORTER FOR MEDICAMENT PUMP

RELATED APPLICATIONS

This application is a continuation of U.S. application Ser. No. 15/705,983 filed Sep. 15, 2017, which claims the benefit of U.S. Provisional Application No. 62/394,806 filed Sep. 15, 2016, each of which is hereby incorporated herein in its entirety by reference.

FIELD OF THE INVENTION

The present invention relates to medical pumps for delivering medicament to a patient and, more specifically, to a vial supporter for securely holding a medicament vial during a cartridge filling process.

BACKGROUND OF THE INVENTION

There are many applications in academic, industrial, and medical fields that benefit from devices and methods that are capable of accurately and controllably delivering fluids, such as liquids and gases, that have a beneficial effect when administered in known and controlled quantities. Such devices and methods can be particularly useful in the medical field where treatments for many patients include the administration of a known amount of a substance at predetermined intervals.

One category of devices for delivering such fluids is that of pumps that have been developed for the administration of insulin and other medicaments for those suffering from both type I and type II diabetes. Some pumps configured as portable infusion devices can provide continuous subcutaneous medicament injection and/or infusion therapy for the treatment of diabetes. Such therapy may include, e.g., the regular and/or continuous injection or infusion of insulin into a person suffering from diabetes and offer an alternative to multiple daily injections of insulin by an insulin syringe or an insulin pen. Such pumps can be ambulatory/portable infusion pumps that are worn by the user and may use replaceable cartridges. Examples of such pumps and various features that can be associated with such pumps include those disclosed in U.S. Patent Application Publication Nos. 2013/0053816, 2013/0324928 and 2013/0331790, and in U.S. Pat. Nos. 8,287,495, 8,573,027 and 8,986,253, each of which is hereby incorporated herein by reference in its entirety.

One type of pump that has been developed is a patch pump, or micro pump. Patch pumps generally are small pumps, typically ambulatory, that are carried directly on the skin under the patient's clothing. Many such pumps are situated directly on the injection site such that no tubing is required to deliver the insulin and/or other medicament to the patient. Other patch pumps can be positioned on the patient's body with a short length of tubing extending to a nearby infusion site. Not unlike other types of pumps, but perhaps more typically, patch pumps can be at least in part disposable, meant to be worn for a period of time such as, e.g., a day or two, and then discarded and replaced by a new patch pump. Other patch pump designs contemplate a disposable component, such as a cartridge that contains medicament, and a reusable or durable component. In such configurations, the disposable and durable components may be joined together by the patient or caregiver in preparation for delivery of the medicament.

Some pumps, including patch pumps, may include medicament cartridges. Such cartridges may be intended for single use only (and thus intended to be filled once) while other cartridges may be intended to be refilled one or more times. Embodiments of the invention disclosed herein cover both such types of cartridge. As such, the terms "fill" and "fellable" should be construed herein to mean cartridges that are intended to be filled once as well as cartridges that are intended to be filled more than once. Moreover, as used herein, the term "fill" encompasses both the act of introducing medicament into a cartridge to its maximum capacity and, in some instances, introducing medicament into a cartridge to less than its maximum capacity. Likewise, the term "fillable" refers to cartridges for use with embodiments of the invention disclosed herein that may be filled to their maximum or to less than their maximum capacity with medicament. To fill a medicament cartridge, a vial or container of medicament typically is coupled to the cartridge of the pump and medicament is transferred from the container to the cartridge. Existing methods of filling pumps can be awkward for a user (patient or caregiver) do to many such cartridges including flexible tubing extending from the cartridge body that is not rigid enough to support a vial of medicament. Thus, users often must carefully hold the cartridge, the container, and any necessary adapters or couplers, while allowing the medicament to transfer from the container to the cartridge. The filling methods are further complicated if the user must assist the cartridge filling process, such as by pulling a fill rod to draw medicament into the cartridge.

SUMMARY OF THE INVENTION

Devices and methods for filling a medicament cartridge of a pump, including a user-wearable, ambulatory infusion pump. A device for supporting a medicament cartridge can comprise a body portion resembling a tray, with recesses disposed therein to support one or more of a cartridge body, cartridge tubing, interconnect fitting, and vial adapter. The recesses of the tray may be shaped to correspond to that component intended to be placed in its respective recess so to provide a visual indication to a user how to couple and align the various components necessary to fill the cartridge.

In one embodiment, a device for supporting a medicament cartridge of an ambulatory infusion pump during a procedure for filling the medicament cartridge with a medicament includes a tray having a cartridge end and a vial end. A cartridge holder can be defined in the tray body adjacent the cartridge end, the cartridge holder comprising a recess in the tray body and having a bottom surface and a perimeter shape generally matching an outer perimeter of a body of the medicament cartridge configured to be retained in the cartridge holder. A fitting holder can be defined in the tray body adjacent the vial end, the fitting holder comprising a recess in the tray body configured to retain an interconnect fitting of the medicament cartridge and having a shape generally matching a shape of the interconnect fitting. A tubing holder can be defined in the tray body, the tubing holder comprising a channel configured to retain a tubing section of the medicament cartridge. In various embodiments, a vial adapter holder can also be defined in the tray body adjacent the fitting holder at the cartridge end of the tray body, the vial adapter comprising a recess in the tray body configured to retain a portion of a vial adapter configured to attach to the interconnect fitting of the medicament cartridge therein.

In another embodiment, a system for filling a medicament cartridge of an ambulatory infusion pump with a medicament can include a medicament cartridge and a cartridge supporter. The medicament cartridge can include a cartridge body defining an outer perimeter, a tubing section extending from the cartridge body and an interconnect fitting at a distal end of the tubing section. The cartridge supporter is configured to support the medicament cartridge during a procedure for filling the medicament cartridge with a medicament. The cartridge supporter can define a tray body having a cartridge end and a vial end and include a cartridge holder recess having a perimeter shape generally matching the outer perimeter of the cartridge body, a fitting holder recess having a shape generally matching a shape of the interconnect fitting and a tubing holder channel configured to retain the tubing section.

In another embodiment, a method of filling a medicament cartridge utilizing a device for supporting a cartridge and/or a vial of medicament is described. The method can include placing a medicament cartridge having a cartridge body and a fitting connected to a tubing portion extending from the cartridge body into a cartridge supporter configured as a tray. A medicament vial containing a medicament can be connected to a vial adapter connected to the fitting. The medicament cartridge can then be filed with the medicament from the medicament vial with the medicament cartridge in a cartridge holder of the tray. After filling the medicament vial can be disconnected from the vial adapter and the medicament cartridge removed from the tray. The vial adapter can be disconnected from the fitting and, in various embodiments, the medicament cartridge can be connected to an ambulatory infusion pump and infusion set for use or a fitting cap inserted into the fitting to store the cartridge for later use.

In a further embodiment, a device for supporting the cartridge and/or a vial of medicament includes a body portion having a means for supporting a tube of the cartridge and a cradle for securely holding a body of the cartridge. The vial supporter may include one or more features that make grasping the supporter easier. The cradle of the vial supporter may include one or more arms which at least partially surround the cartridge when the cartridge is coupled to the vial supporter during a filling procedure.

The above summary is not intended to describe each illustrated embodiment or every implementation of the subject matter hereof. The figures and the detailed description that follow more particularly exemplify various embodiments.

BRIEF DESCRIPTION OF THE DRAWINGS

Subject matter hereof may be more completely understood in consideration of the following detailed description of various embodiments in connection with the accompanying figures, in which.

Figure 1:
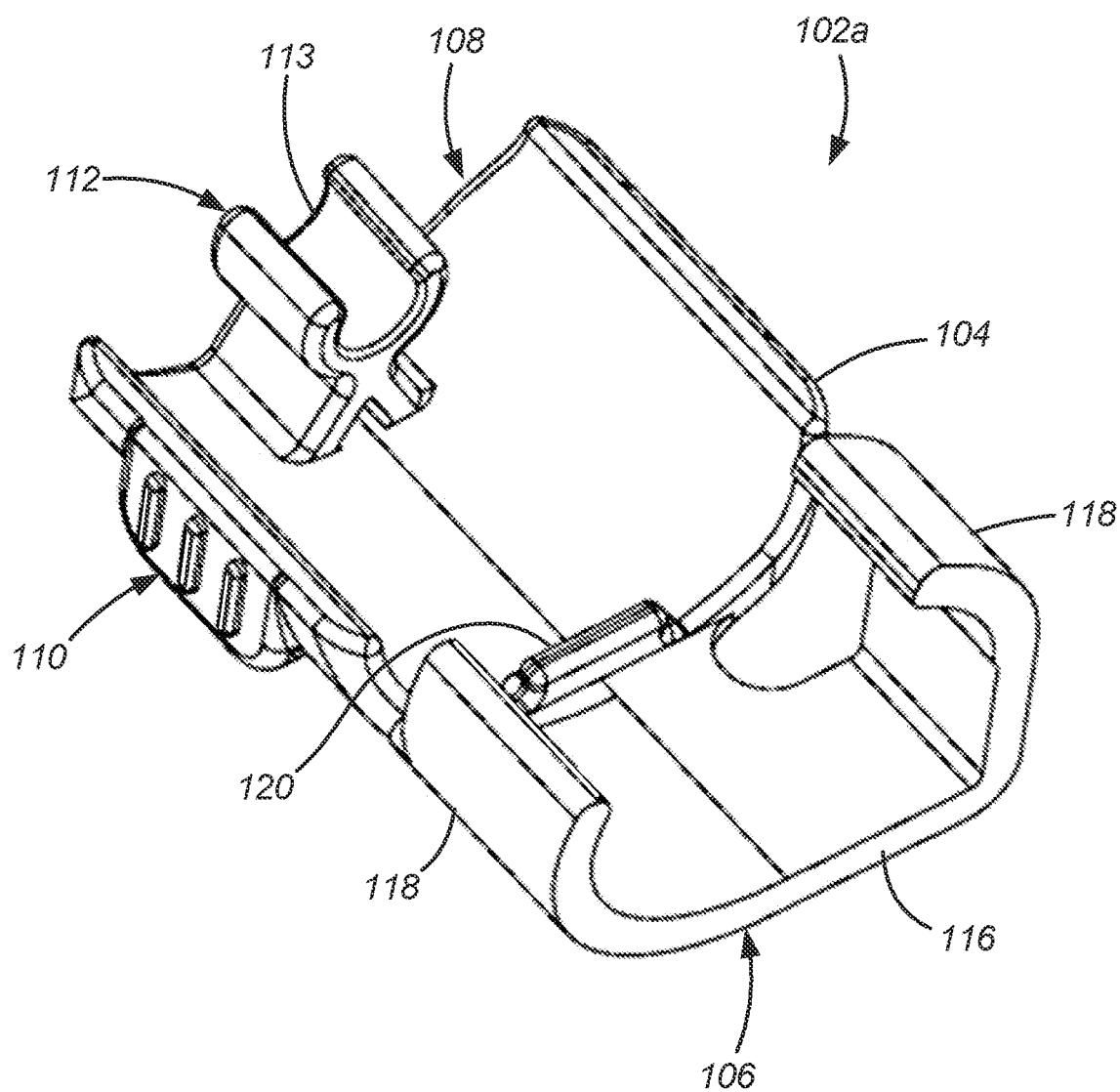
FIG. 1 is a perspective view of a vial supporter according to an embodiment of the present invention.
Figure 2:
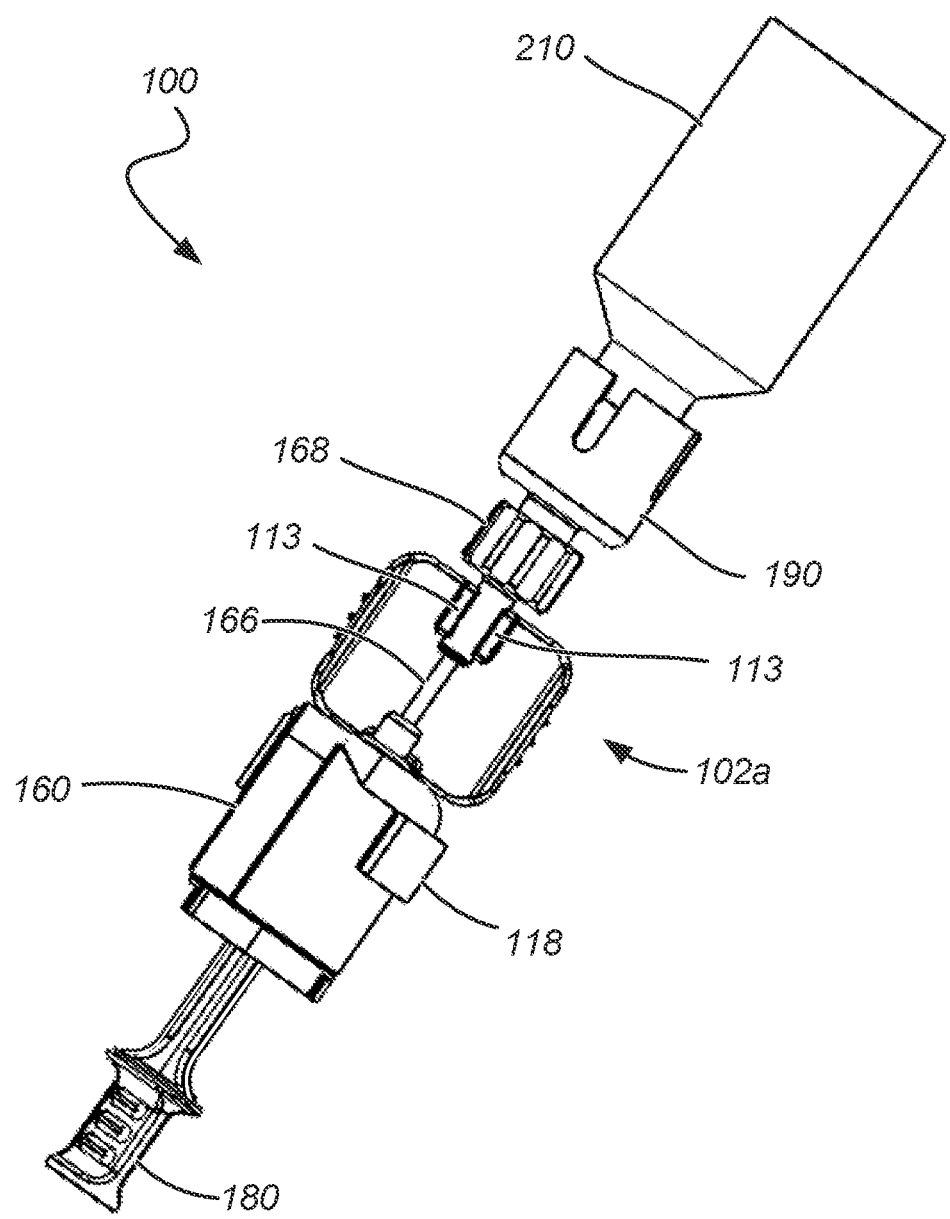
FIG. 2 is a top plan view of the vial supporter of FIG. 1, coupled with a vial adapter, a container of medicament and a fillable cartridge.
Figure 3:
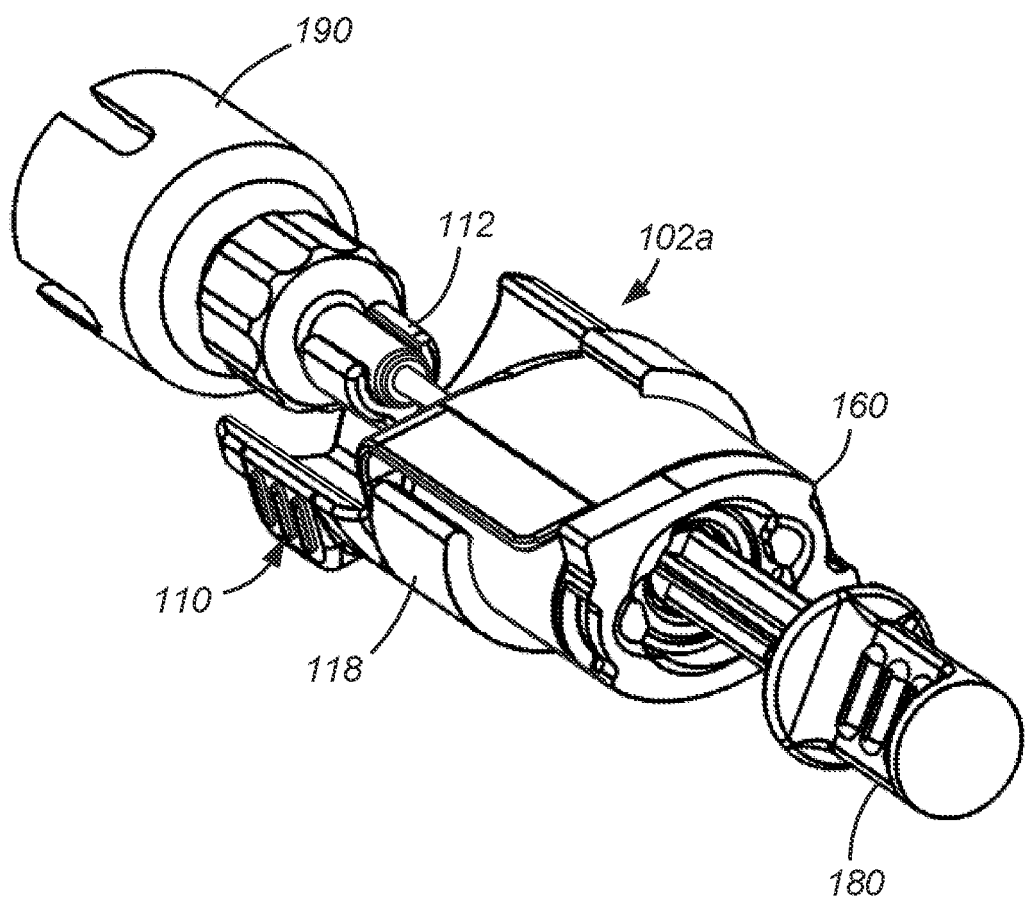
FIG. 3 is a perspective view of FIG. 2 without the container of medicament.
Figure 4:
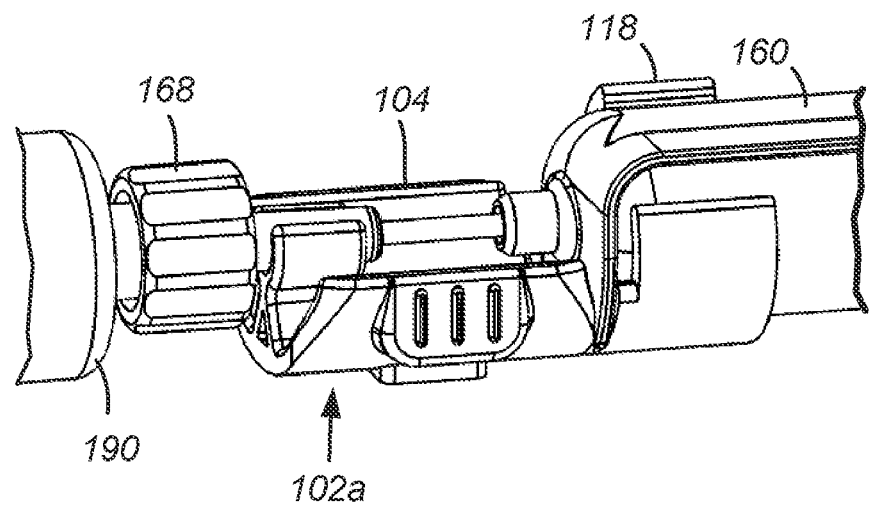
FIG. 4 is a detail perspective view of the vial supporter of FIG. 3.

While various embodiments are amenable to various modifications and alternative forms, specifics thereof have been shown by way of example in the drawings and will be described in detail. It should be understood, however, that the intention is not to limit the claimed inventions to the particular embodiments described. On the contrary, the intention is to cover all modifications, equivalents, and alternatives falling within the spirit and scope of the subject matter as defined by the claims.

DETAILED DESCRIPTION OF THE DRAWINGS

The following detailed description should be read with reference to the drawings in which similar elements in different drawings are numbered the same. The drawings, which are not necessarily to scale, depict illustrative embodiments and are not intended to limit the scope of the invention.

Described herein are devices and methods for securely supporting components associated with fillable cartridges for patch pumps.

Referring to FIGS. 1-4, one embodiment of a system 100 is depicted, which includes a vial supporter 102a, a cartridge 160, a fill rod 180, an adapter 190, and/or a medicament vial 210. System 100 may include all, or less than all of the components depicted in FIGS. 1-4. Vial supporter 102a can generally include a body portion 104 having a first end 106, a second end 108, and one or more features 110 to facilitate grasping vial supporter 102a by a user during a cartridge filling process and provide a guide as to a desired position to grasp supporter 102a. First end 106 includes a cartridge cradle 116 or other suitable means configured for receiving a fillable cartridge 160, and one or more arms 118 or other suitable means configured for coupling with and supporting cartridge 160. Arms 118 are arranged to facilitate easy installation and removal of cartridge 160 while also securely retaining cartridge 160 during filling. As depicted in FIGS. 1-4, each of arms 118 may be uniquely shaped and sized but in other embodiments arms 118 may be symmetrically shaped and/or size, either with respect to an individual arm 118 or between or among two or more arms, in any combination. A stop 120 may be included to help locate cartridge 160 in supporter 102a and prevent movement of cartridge 160 toward second end 108 during, e.g., a cartridge filling process. Vial supporter 102a may also have one or more features (not pictured) to limit movement of cartridge 160 towards first end 106 during, e.g., a cartridge filling process (when fill rod 180 described below is moved or pulled towards first end 106).

Second end 108 may include a cradle 112 configured to couple with and support a tubing section 166 of cartridge 160. Alternately, cradle 112 may be configured to support an interconnect fitting 168 of cartridge 160 in addition to, or instead of, tubing section 166. As depicted in FIGS. 1-4, cradle 112 comprises a raised cradle portion defining an aperture or region 113 into which tubing 166 may be snapped or otherwise put in place. The open area defined by edges 113 of the cradle facilitates grasping or otherwise accessing the fitting 168 or tubing 166 when a user wishes to remove them from vial supporter 102a. In addition to a single cradle 112, multiple cradles may be utilized, and other configurations of element 112 that support and/or hold tubing section 166 and/or interconnect fitting 168 and facilitate grasping the fitting and tubing are within the scope of the invention.

Vial supporter 102a is configured to securely retain and support cartridge 160 such that cartridge 160 can be easily filled. Body 162 of cartridge 160 is held in cartridge cradle 116 of vial supporter 102a, while tubing section 166 is held in cradle 112 of vial supporter 102a. A fill rod 180 is coupleable to cartridge 160, and a vial adapter 190 is coupleable to interconnect fitting 168 of cartridge 160. Vial adapter 190 facilitates connection between a medicament vial 210 and cartridge 160. While filling cartridge 160 using vial supporter 102a, a user need not grasp or hold vial 210, as vial 210 is sufficiently held in place with vial supporter 102a.

In operation, vial supporter 102a provides a stable and secure arrangement of cartridge 160, tubing 166, adapter 190, and vial 210, and prevents any misalignment or disconnection between these components while filling cartridge 160.

Figure 5:
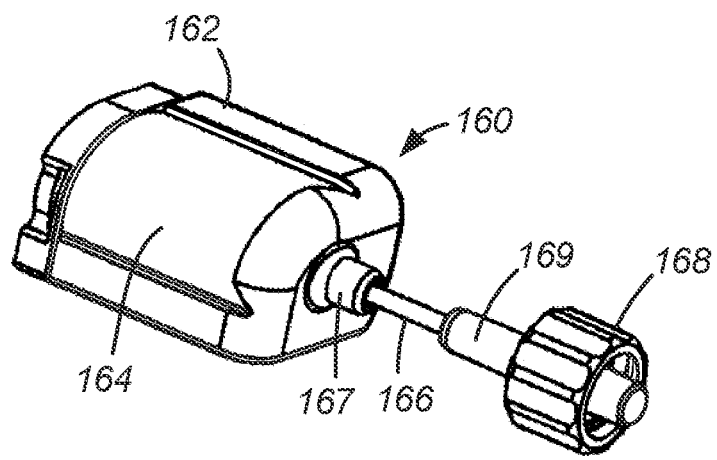
FIG. 5 is a perspective view of a fillable cartridge.
Figure 13:
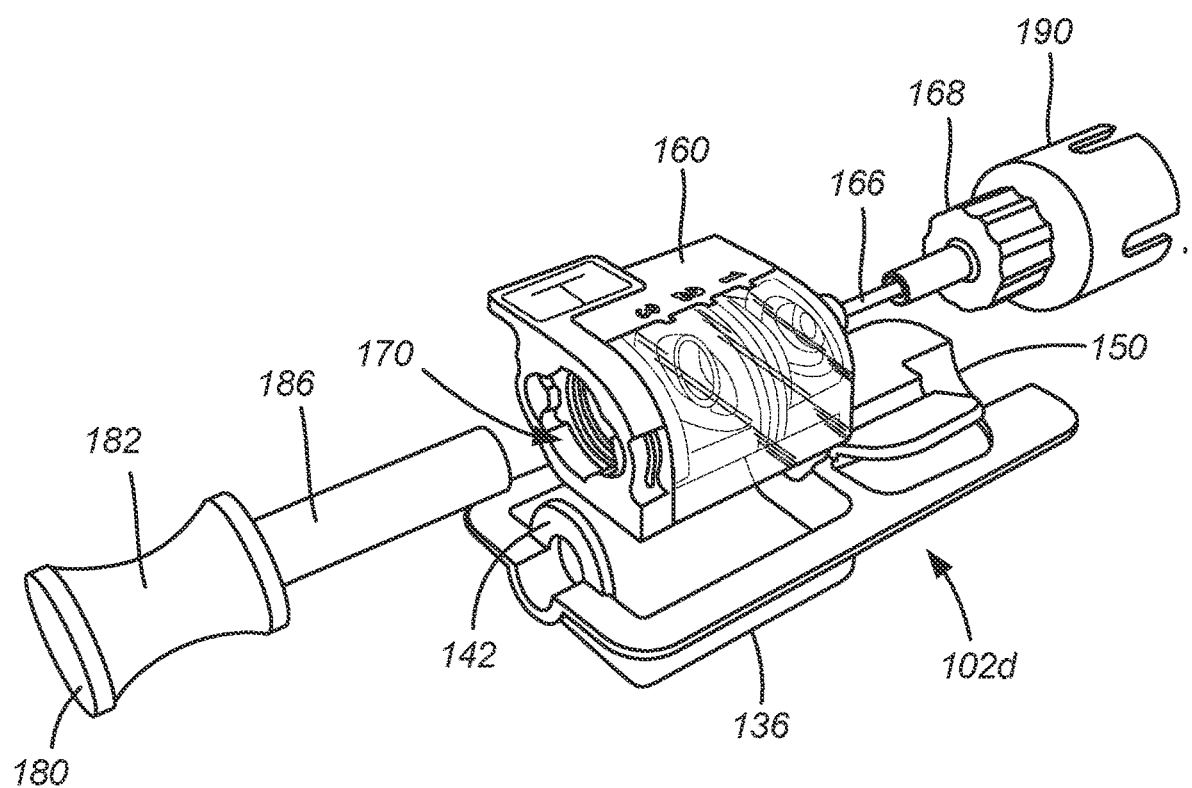
FIG. 13 is an exploded perspective view of the supporter of FIG. 12.

Cartridge 160 is depicted in FIG. 5, and includes body 162, a reservoir 164, tubing section 166 and interconnect fitting 168. Cartridge 160 and/or the embodiments of vial supporters described herein can be configured such that reservoir 164 is visible when cartridge 160 is coupled with a vial supporter, such that a user can determine the level of medicament in cartridge 160 and/or visually inspect for bubbles. During a filling procedure or method, fitting 168 provides a connection for vial 210. During operation of a pump, fitting 168 provides a connection to a medicament administration set (not depicted). Cartridge 160 also includes a port 170 for fill rod 180, as best depicted in FIG. 13.

Figure 6:
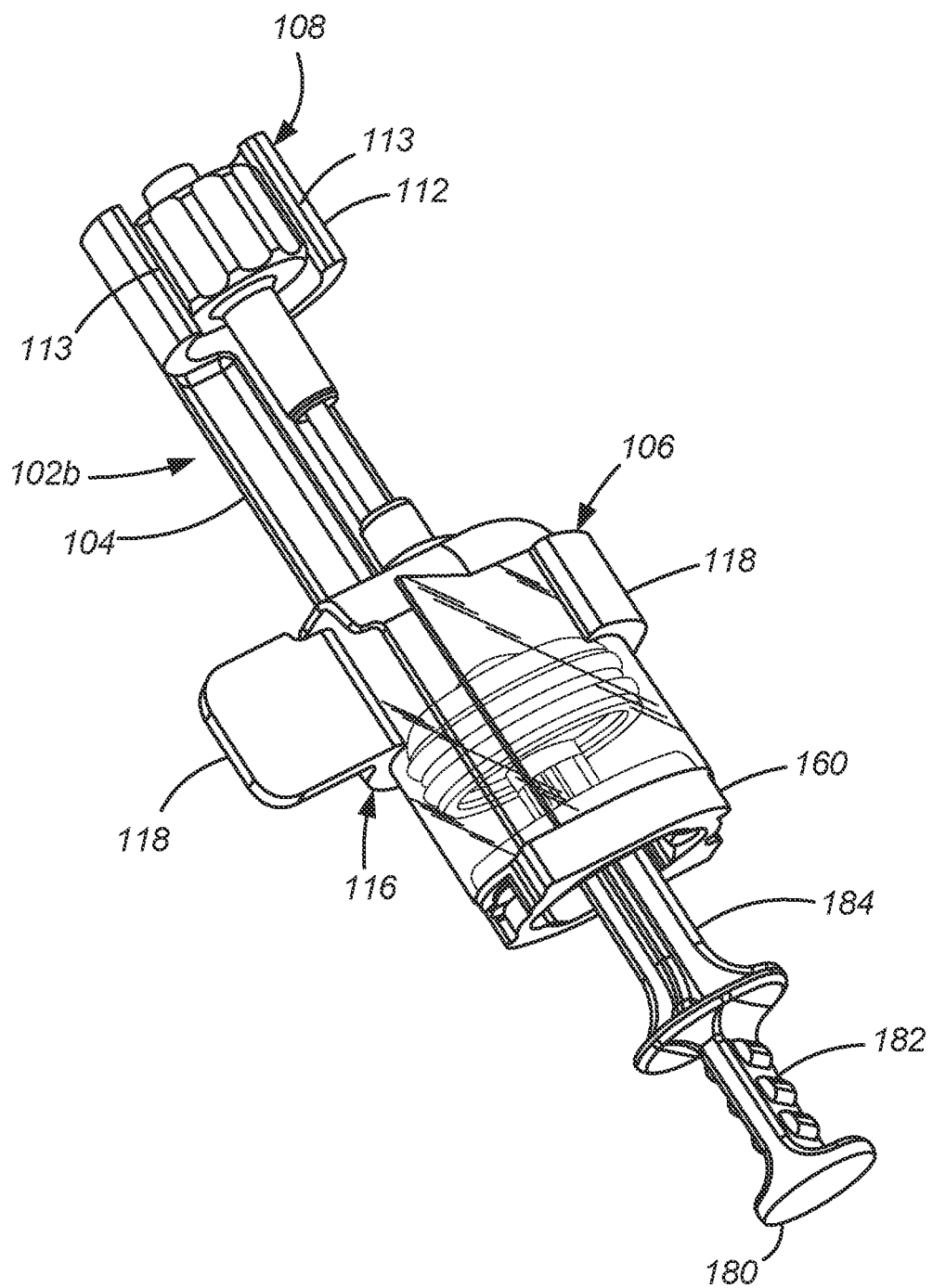
FIG. 6 is a perspective view of a vial supporter according to another embodiment of the present invention.
Figure 7:
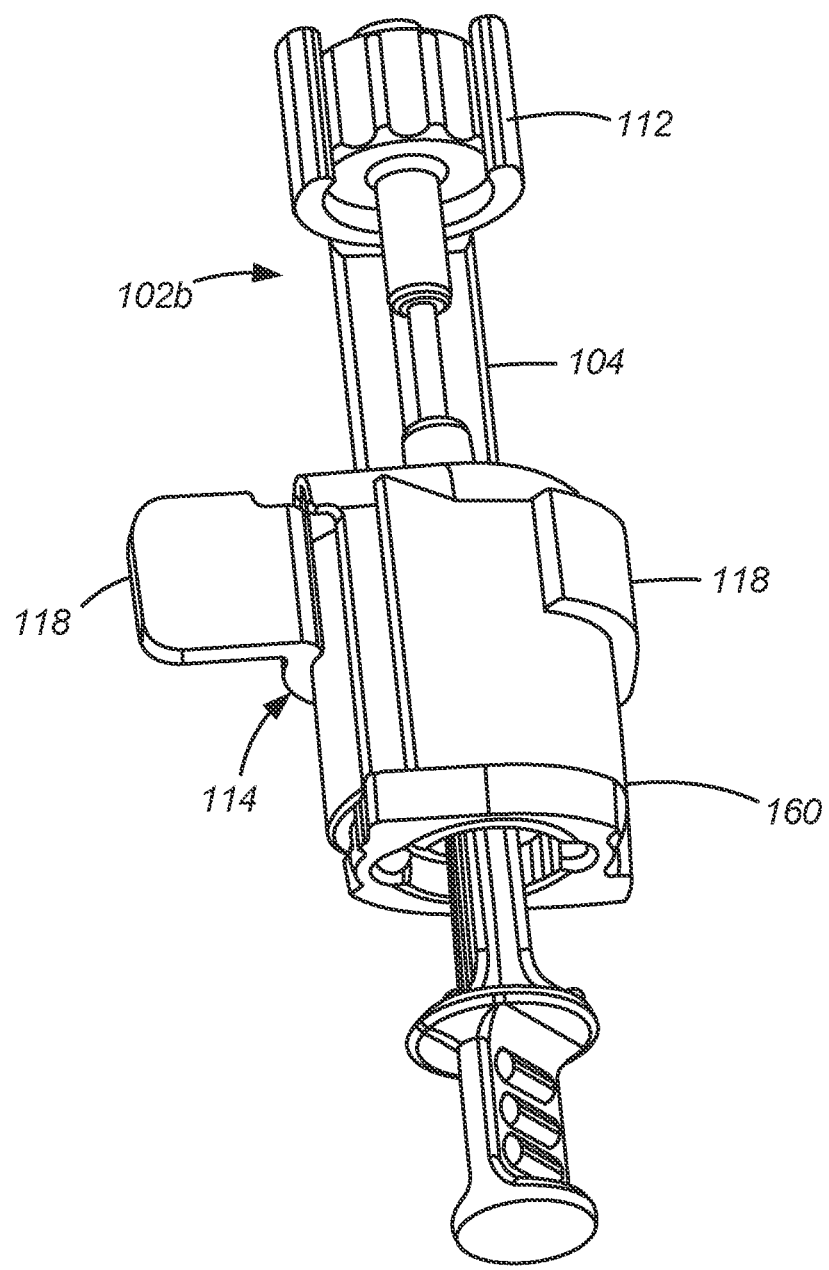
FIG. 7 is another perspective view of the vial supporter of FIG. 6.
Figure 8:
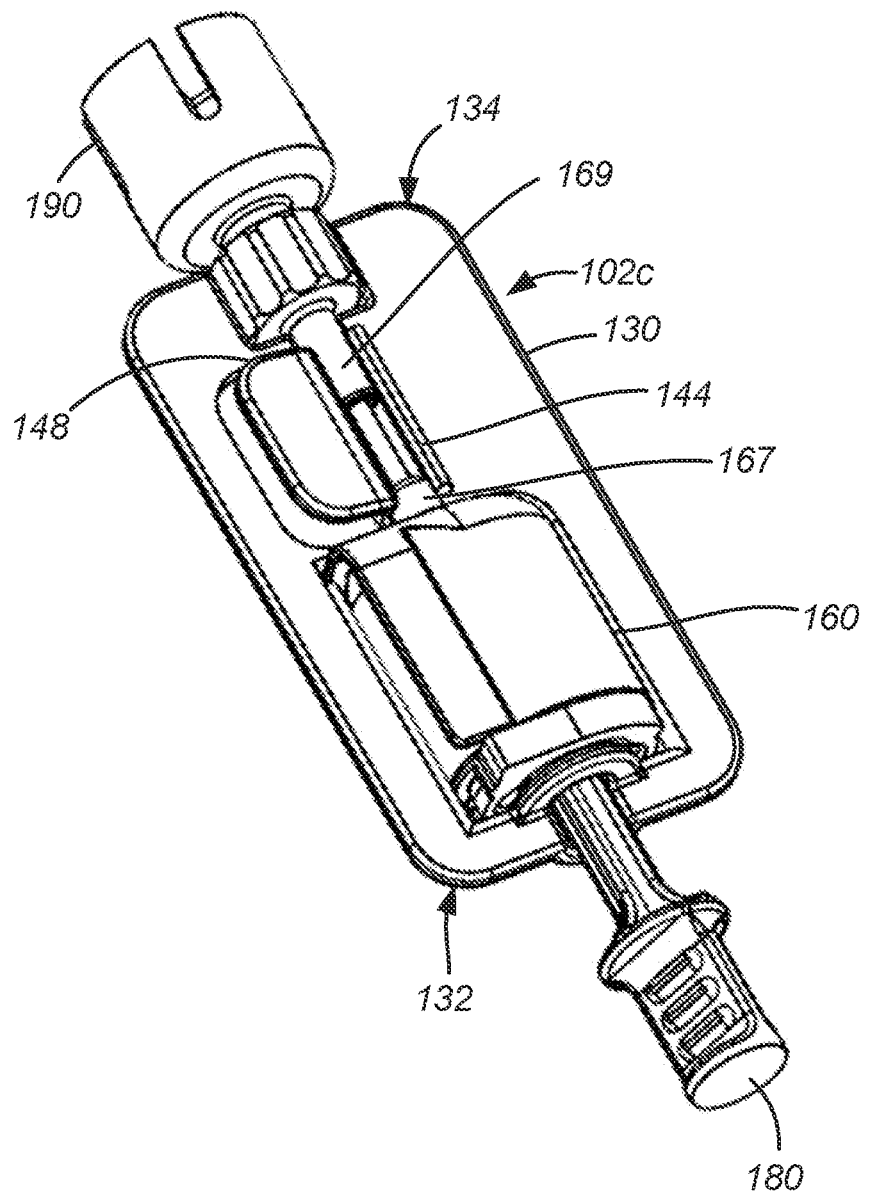
FIG. 8 is a perspective view of a cartridge and/or vial supporter according to another embodiment of the present invention, coupled with a vial adapter and a fillable cartridge.
Figure 9:
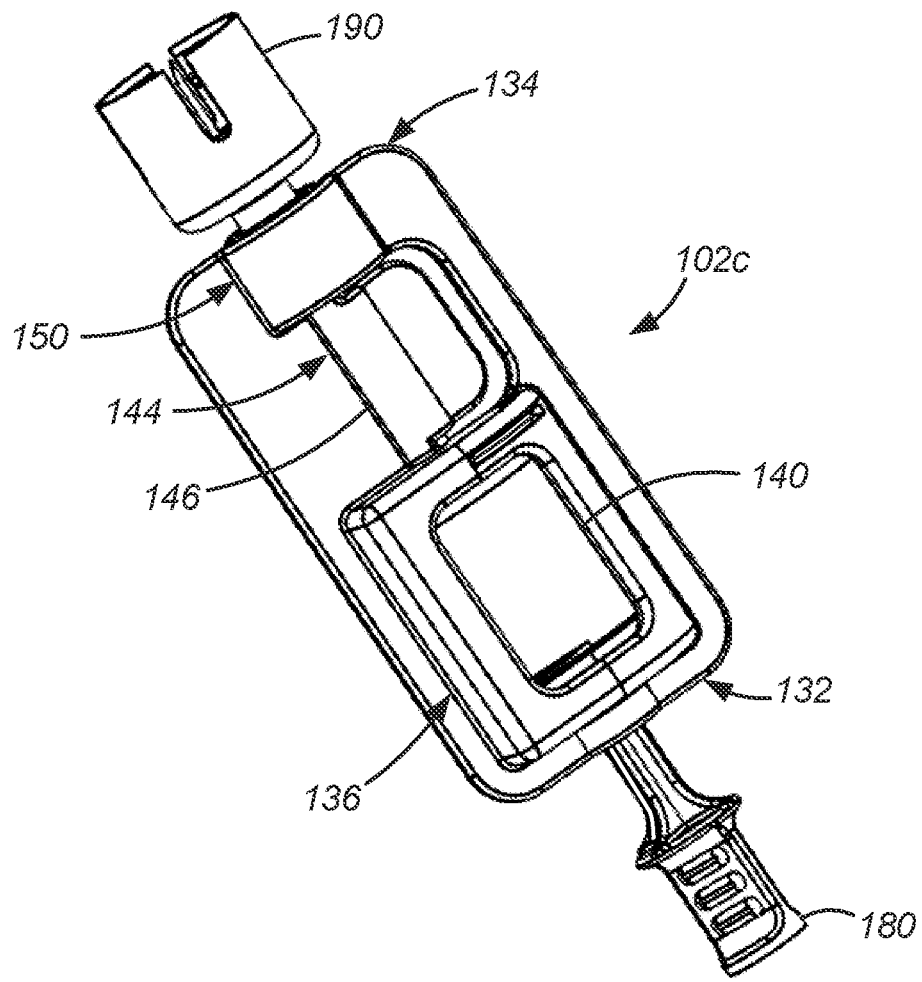
FIG. 9 is a view of the underside of FIG. 8.
Figure 10:
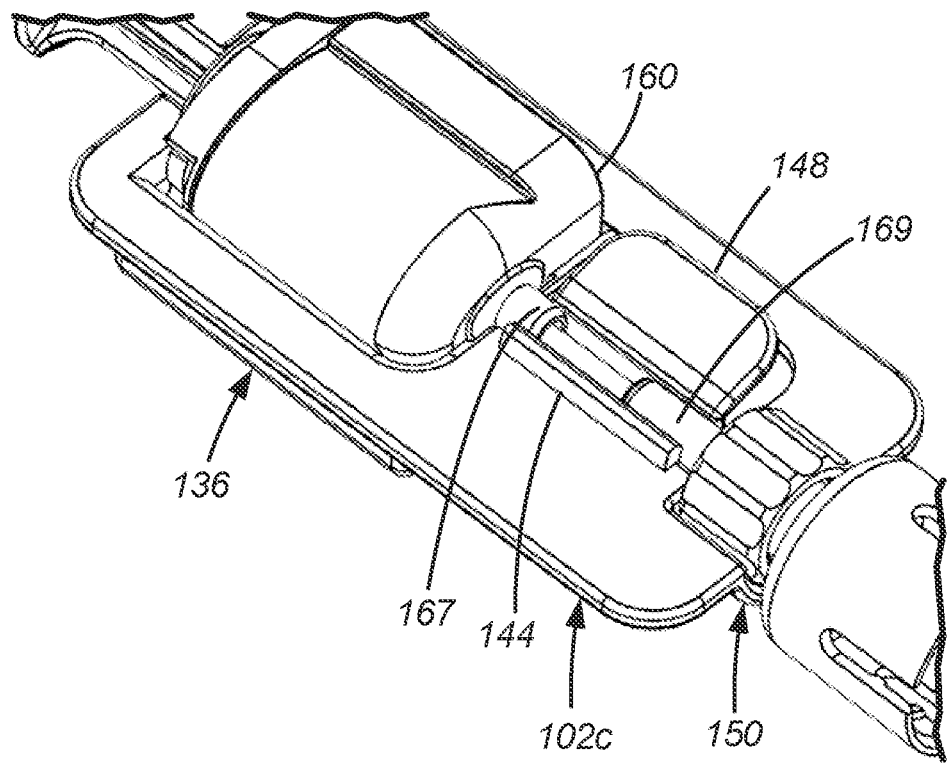
FIG. 10 is a detail view of the supporter of FIG. 8.
Figure 11:
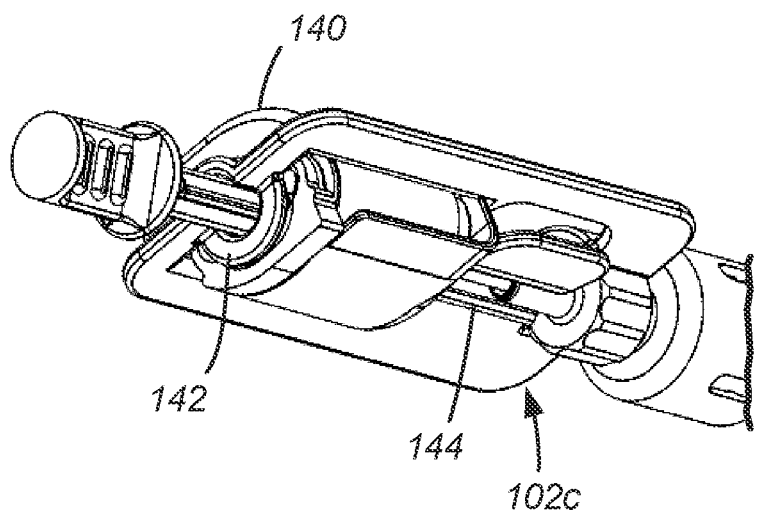
FIG. 11 is another perspective view of the supporter of FIG. 8.

Referring now to FIGS. 6-7, a vial supporter 102b is depicted. Vial supporter 102b includes components similar to those in vial supporter 102a described previously. Thus, vial supporter 102b can generally include a body portion 104 having a first end 106 and a second end 108. First end 106 includes a cartridge cradle 116 or other suitable means configured for receiving a fillable cartridge 160, and one or more arms 118 or other suitable means configured for coupling with and supporting cartridge 160. Arms 118 are arranged to facilitate easy installation and removal of cartridge 160 while also securely retaining cartridge 160 during cartridge filling. As depicted in FIGS. 6-7, each of arms 118 may be uniquely shaped and sized but in other embodiments arms 118 may be symmetrically shaped and/or sized, either with respect to an individual arm 118 or between or among two or more arms, in any combination. A stop (not pictured) may be included to help locate cartridge 160 in supporter 102b and prevent movement of cartridge 160 toward second end 108 during a cartridge filling process. Vial supporter 102b may also have one or more features (not pictured) to limit movement of cartridge 160 towards first end 106 during, e.g., a cartridge filling process (when fill rod 180 is moved or pulled towards first end 106).

Second end 108 may include a cradle 112 configured to couple with and support an interconnect fitting 168 of cartridge 160. Alternately, cradle 112 may be configured to support a tubing section 166 of cartridge 160 in addition to, or instead of, fitting 168. As depicted in FIGS. 6-7, cradle 112 comprises a raised cradle portion defining an aperture or region 113 into which fitting 168 may be snapped or otherwise put in place. The open area defined by edges 113 of the cradle facilitates grasping or otherwise accessing the fitting 168 or tubing 166 when a user wishes to remove them from vial supporter 102a. In addition to a single cradle 112, multiple cradles may be utilized, and other configurations of element 112 that support and/or hold tubing section 166 and/or interconnect fitting 168 and facilitate grasping the fitting and tubing are within the scope of the invention.

Vial supporter 102b is configured to securely retain and support cartridge 160 such that cartridge 160 can be easily filled. Body 162 of cartridge 160 is held in cradle 116 of vial supporter 102b, while tubing section 166 is held in cradle 112 of vial supporter 102b. A fill rod 180 is coupleable to cartridge 160, and a vial adapter 190 is coupleable to interconnect fitting 168 of cartridge 160. Vial adapter 190 facilitates connection between a medicament vial 210 and cartridge 160. While filling cartridge 160 using vial supporter 102b with medicament, a user need not grasp or hold vial 210, as vial 210 is sufficiently held in place by vial supporter 102b.

For any of the embodiments depicted herein, fill rod (or plunger handle) 180 can generally include a handle portion 182 configured for grasping by a user, a shaft portion 184, and a threaded portion 186 as depicted in, e.g., FIG. 13.

Referring now to FIGS. 8-11, another embodiment of a cartridge and/or vial supporter 102c is depicted. Supporter 102c can generally include a tray body 130 having a cartridge end 132 and a vial end 134, a cartridge holder 136, a tubing holder 144, and an interconnect fitting holder 150. Tray body 130 is shaped to ease handling during the process of filling a cartridge with medicament and, in some embodiments, is configured to be held by a user in a single hand. Cartridge holder 136 comprises a recess, channel, cut-out, relief or similar feature into which a cartridge 160 may be at least partially placed or nested. Cartridge holder 136 is sized and shaped to snugly receive cartridge 160, including having a perimeter shape generally matching or approximating an outer perimeter shape of the cartridge. Cartridge holder 136 may also define an aperture or window 140 configured to allow visual inspection of reservoir 164 when cartridge 160 is placed in holder 136 as well as to aid in removal of the cartridge by allowing the user to press on that side of the cartridge to urge the cartridge out of the cartridge holder. By visually inspecting cartridge 160, either through window 140 or the opposite, fully exposed side of the cartridge, a user can determine whether there are air bubbles in the cartridge that need to be removed. In addition, the cartridge can comprise a clear material in the reservoir area where the medicament is contained and can, in some embodiments, include graduated markings delineating volume levels in the reservoir, such that visual inspection can further determine the volume of medicament in the cartridge. Also included in supporter 102c is a ring or other similar retention means 142 through which fill rod 180 may be inserted or placed. Ring 142 assists in retaining cartridge 160 securely in place when fill rod 180 is installed because in the depicted embodiment cartridge 160 cannot be removed if the fill rod extends through the ring and is attached to the cartridge.

Tubing holder 144 is configured to retain and support tubing section 166 of cartridge 160, and can generally include a channel or nest 146 and one or more tabs 148. Channel 146 is preferably sized and shaped to provide a secure fit, such as a "snap" fit, with one or more of a reduced diameter portion 169 of interconnect fitting 168 and a portion 167 of cartridge 160. To remove tubing 166 from channel 146, a user may push down on tab 148, thereby flexing the material and opening channel 146, allowing tubing 166 to be removed. Interconnect fitting holder 150 may comprise a recess or cradle or one or more other configurations and/or features sized and shaped to receive interconnect fitting 168 of cartridge 160. Furthermore, interconnect fitting holder 150 can have additional features (not shown) to prevent undesirable rotation of the interconnect fitting 168 when, e.g., a user is detaching interconnect fitting 168 from vial adapter 190 (such as, e.g., by unscrewing). In various embodiments, the recess defining interconnect fitting holder 150 may be contiguous and/or continuous with the channel 146 defining tubing holder, which in turn may be contiguous and/or continuous with the recess defining cartridge holder. Thus, in some embodiments, a single continuous recess may define all of the respective holders, with a varying outer perimeter that matches the shape of the respective component held in each of the holders (additionally optionally including vial adapter holder 151, discussed below with respect to FIGS. 19-20) and/or a varying depth based on the respective component.

Each of cartridge holder 136, tubing holder 144, and interconnect fitting holder 150 is configured to provide a user with the ability readily to perform a quick visual and/or tactile confirmation that cartridge 160 and associated components are properly positioned and aligned before beginning a cartridge filling process. While filling cartridge 160 using supporter 102c, a user need not grasp or hold vial 210, as vial 210 is sufficiently held in place with supporter 102c. This results in significant improvement in the user's experience by reducing the complexity and increasing the simplicity of a key aspect of using medicament pumps as described herein.

Figure 12:
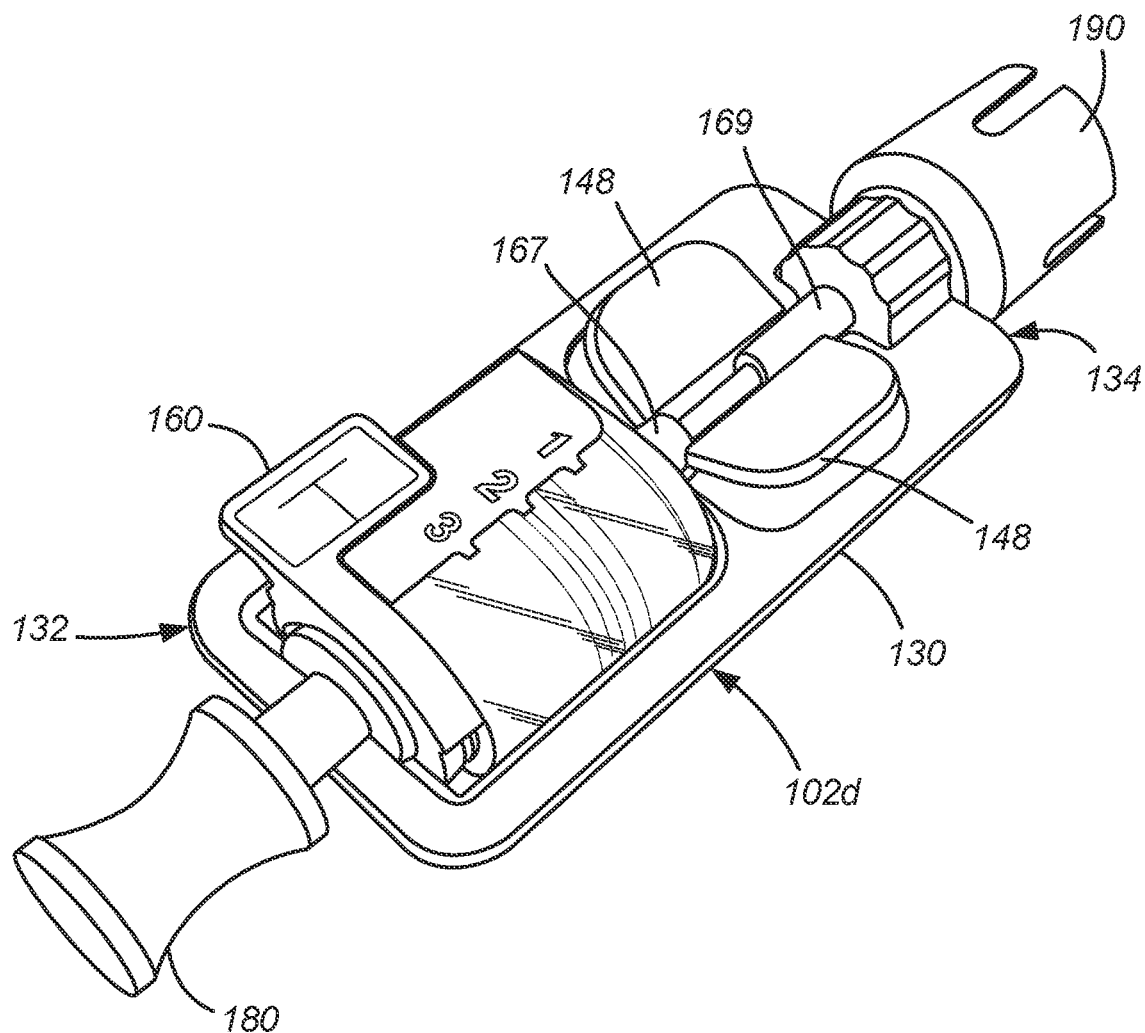
FIG. 12 is a perspective view of a cartridge and/or vial supporter according to another embodiment of the present invention, coupled with a vial adapter and a fillable cartridge.
Figure 14:
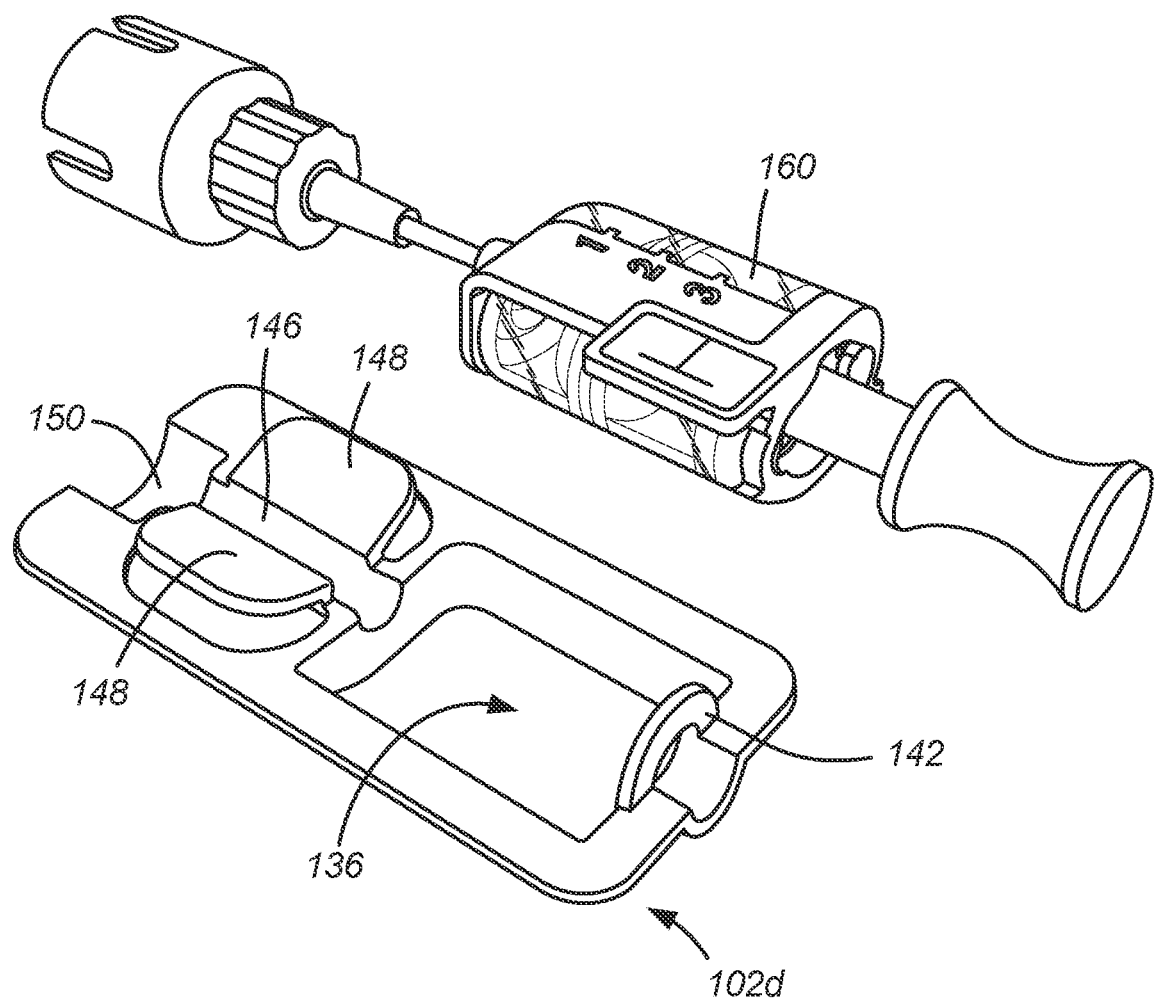
FIG. 14 is a perspective view of the supporter of FIG. 12.

Referring now to FIGS. 12-14, a cartridge and/or vial supporter 102d is depicted. Supporter 102d includes many components similar to those associated with supporter 102c described previously. Thus, supporter 102d can generally include a tray body 130 having a cartridge end 132 and a vial end 134, a cartridge holder 136, a tubing holder 144, and an interconnect fitting holder 150. Cartridge holder 136 comprises a recess, channel, cut-out, relief or similar feature into which a cartridge 160 may be at least partially placed or nested. Cartridge holder 136 is sized and shaped to snugly received cartridge 160. Cartridge holder 136 may also include an aperture or window 140 which is configured to allow visual inspection of reservoir 164 when cartridge 160 is placed in holder 136. Also included in supporter 102d is a ring or other similar retention means 142 through which shaft 184 of fill rod 180 may be inserted or placed. Ring 142 cooperates with fill rod 180 to retain cartridge 160 securely in place when fill rod 180 is installed.

Tubing holder 144 is configured to retain and support tubing section 166 of cartridge 160, and can generally include a channel or nest 146 and one or more tabs 148. Channel 146 is preferably sized and shaped to provide a secure fit with tubing 166. To remove tubing 166 from channel 146, a user may push down on tab 148, thereby flexing the material and opening channel 146, allowing tubing 166 to be removed. Tabs 148 as shown in FIGS. 12-14 can clip over one or more of an end portion 167 of the cartridge 160 and an end portion 169 of the interconnect fitting 168 to securely hold one or both components in place. Downward pressure on tabs 148 can release the components secured therein. Interconnect fitting holder 150 may comprise a recess or cradle (which may or may not be contiguous with channel or nest 146), or other similar configuration which is sized and shaped to receive interconnect fitting 168 of cartridge 160. In some embodiments, the fitting holder 150 can be shaped to prevent turning of the interconnect fitting 168 when it is disposed in the fitting holder 150.

Each of cartridge holder 136, tubing holder 144, and interconnect fitting holder 150 is configured to provide a user with the ability readily to perform a quick visual and/or tactile confirmation that cartridge 160 and associated components are properly positioned and aligned before beginning a cartridge filling process. This results in significant improvement in the user's experience and reduces the complexity and simplicity of a key aspect of using medicament pumps as described herein. While filling cartridge 160 using supporter 102d, a user need not grasp or hold vial 210, as vial 210 is sufficiently held in place with supporter 102d.

Figure 15:
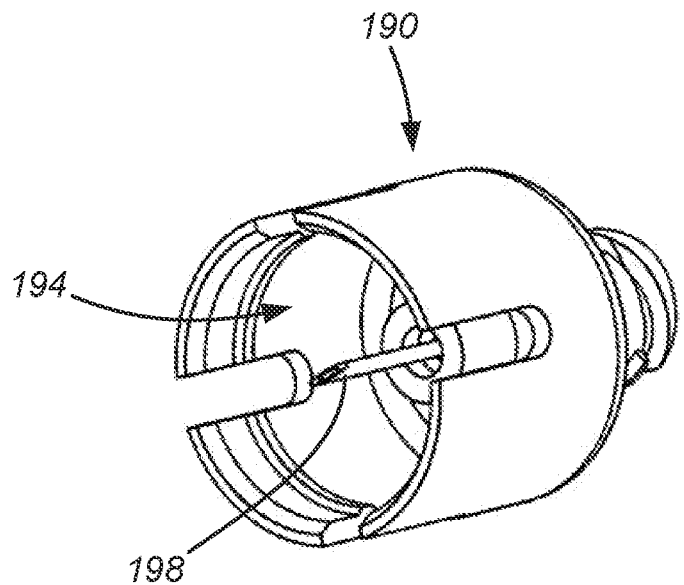
FIG. 15 is a perspective view of a vial adapter according to an embodiment of the invention.
Figure 16:
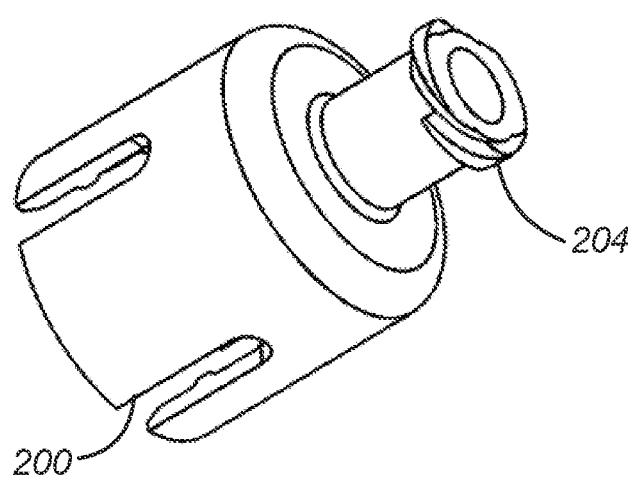
FIG. 16 is another perspective view of the vial adapter of FIG. 15.
Figure 17:
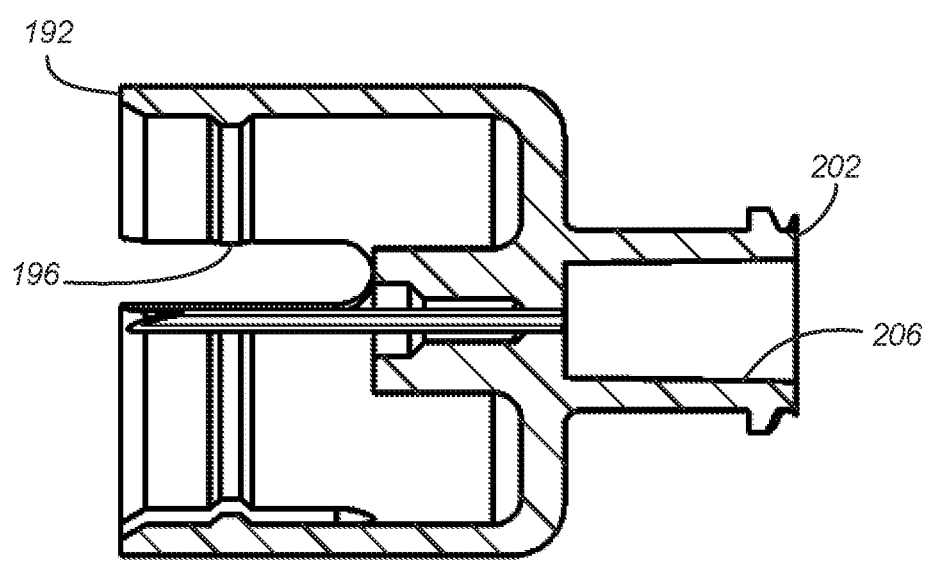
FIG. 17 is a cutaway side view of the vial adapter of FIG. 15.

Referring now to FIGS. 15-17, an embodiment of a vial adapter 190 is depicted. This embodiment can generally include a vial end 192, and a cartridge end 202, a bore 194 for receiving vial 210, a retention feature 196 disposed within bore 194, a needle 198 for puncturing vial 210 and allowing fluid such as medicament to flow therethrough, and one or more reliefs 200. Cartridge end 202 includes a vial adapter fitting 204 configured for coupling to the fitting 168 of cartridge 160 and a bore 206 which may be straight or tapered so to improve sealing when vial adapter 190 is coupled with fitting 168. Other profiles of bore 206, including combinations of straight and tapered and/or curved profiles, may be used as desired. Fitting 204 may be a Luer-type fitting, a proprietary fitting, or other desired style of fitting. In use, vial 210 is placed into bore 194, engaging with retention feature 196. Reliefs 200 allow vial adapter 190 to flex slightly when vial 210 is installed or removed, thus facilitating secure use.

FIGS. 19A-19B and 20A-20B depict another embodiment of a cartridge and/or vial supporter 102e. Similar to the embodiment of, e.g., FIGS. 8-11, supporter 102e is configured with a tray body 130 having a cartridge end 132 and a vial end 134. Tray body 130 includes cartridge holder 136 configured to contain a cartridge 160 therein, a tubing holder 144 and a fitting holder 150. Each of these components is configured and functions substantially similarly to the embodiments described above. In addition, tray 130 includes a vial adapter holder 151 defined by a recess, channel, cut-out, relief or similar feature at vial end 134 of trail body 130 adjacent fitting holder 150 and adapted to receive a fitting end 191 of a vial adapter 190. Because fitting end 191 of vial adapter 190 is configured to connect to the interconnect fitting 168 of cartridge, vial adapter holder 151 will generally be positioned adjacent the fitting holder 150 at vial end 134 of tray body 130. In some embodiments, vial adapter holder 151 can be formed contiguously and/or continuously with interconnect fitting holder 150. In various embodiments, vial adapter holder 151 can be provided with a configuration that prevents rotation of vial adapter 190 and thereby prevents unscrewing of fitting end 191 of the vial adapter 190 from cartridge fitting 168 when the components are nested in the tray body 130. In the depicted embodiment, fitting end 191 of the vial adapter is provided with a hexagonal configuration and vial adapter holder 151 has a corresponding partial-hexagonal shape matching the configuration of the fitting end to prevent such rotation, but in other embodiments any other matching shapes that prevent rotation could be used.

Also in the embodiment depicted in FIGS. 19A-20B, a fitting retention tab 148 interfaces with interconnect fitting 168 to retain the fitting in the tray body 130. Fitting 168 can be press fit into fitting holder 150 to form an audible "snap" fit as described above with fitting retention tab 148 physically engaging fitting 168 to hold fitting 168 in fitting holder 150. This physical engagement can then be released by pressing on fitting retention tab 148 to enable removal of fitting 168 from fitting holder 150. This embodiment also includes a cartridge retention tab 149, which can be seen in the partial cross-sectional view of FIG. 20C. When cartridge 130 is inserted into cartridge holder 136, a bottom wall portion 147 of cartridge is seated beneath cartridge retention tab 149. This prevents direct upward movement of cartridge 160 out of cartridge holder 136. Cartridge 160 can be removed by first tilting the opposite end of cartridge 160 (adjacent the tubing portion 144) upward, and then sliding bottom wall portion 147 away from cartridge retention tab 149. Fitting retention tab or tabs 148, along with cartridge holder 136 and cartridge retention tab 149 and/or the combination of fill rod 180 and ring 142 (in embodiments described above), generally prevent both forward and backward movement and upward movement of the components contained in tray body 130 during the cartridge filling process.

Figure 19A:
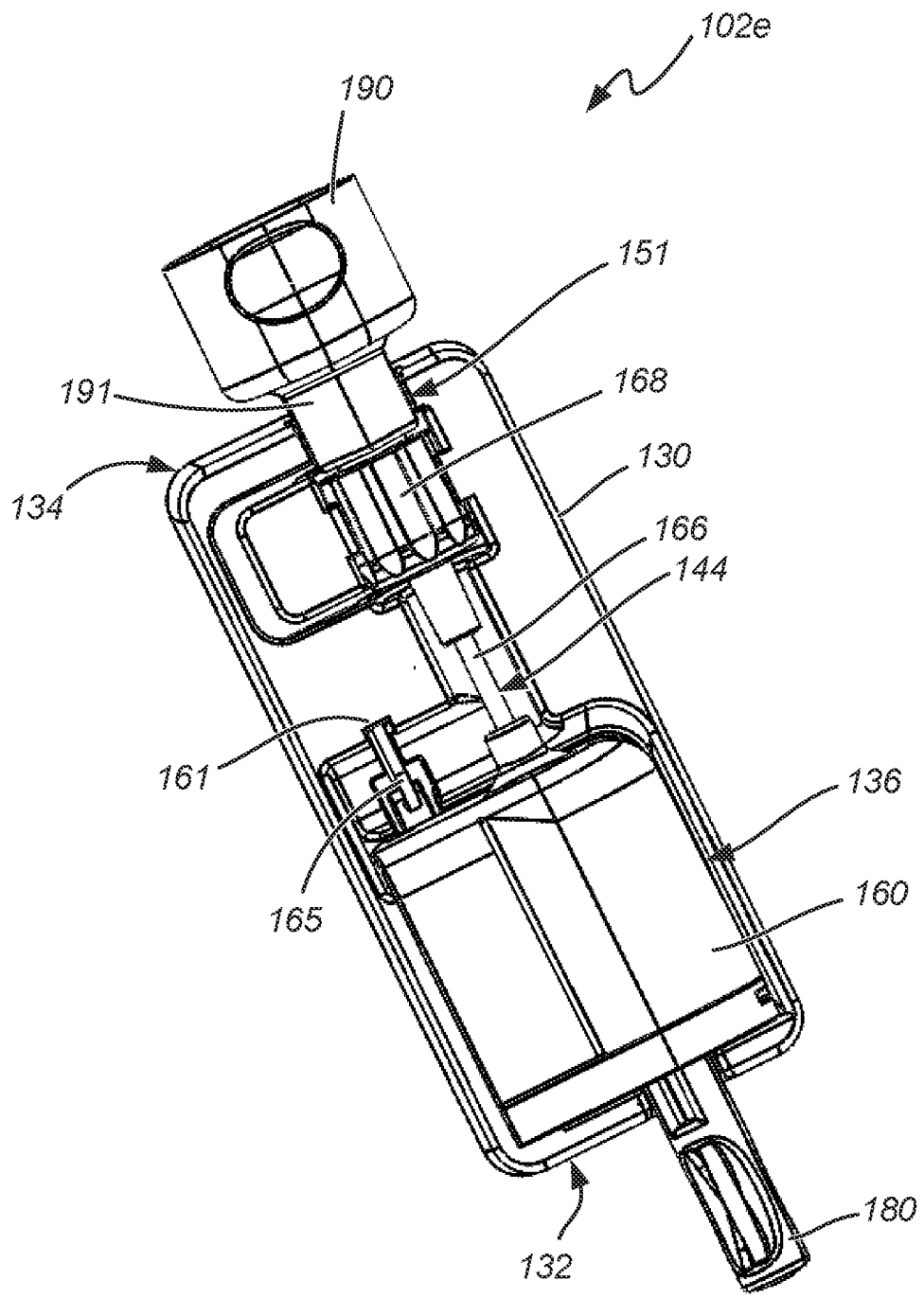
FIGS. 19A-19B and 20A-20B are perspective views of a cartridge and/or vial supporter according to another embodiment of the present invention.
Figure 19B:
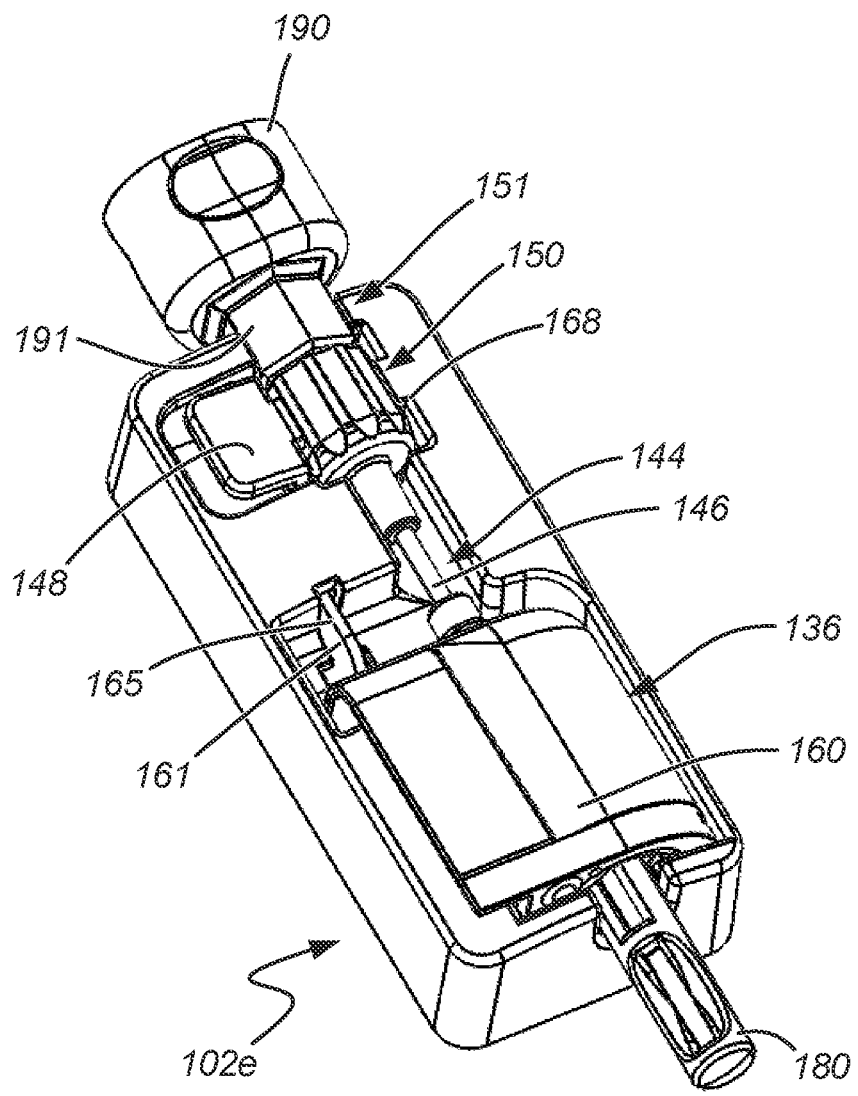
Figure 20A:
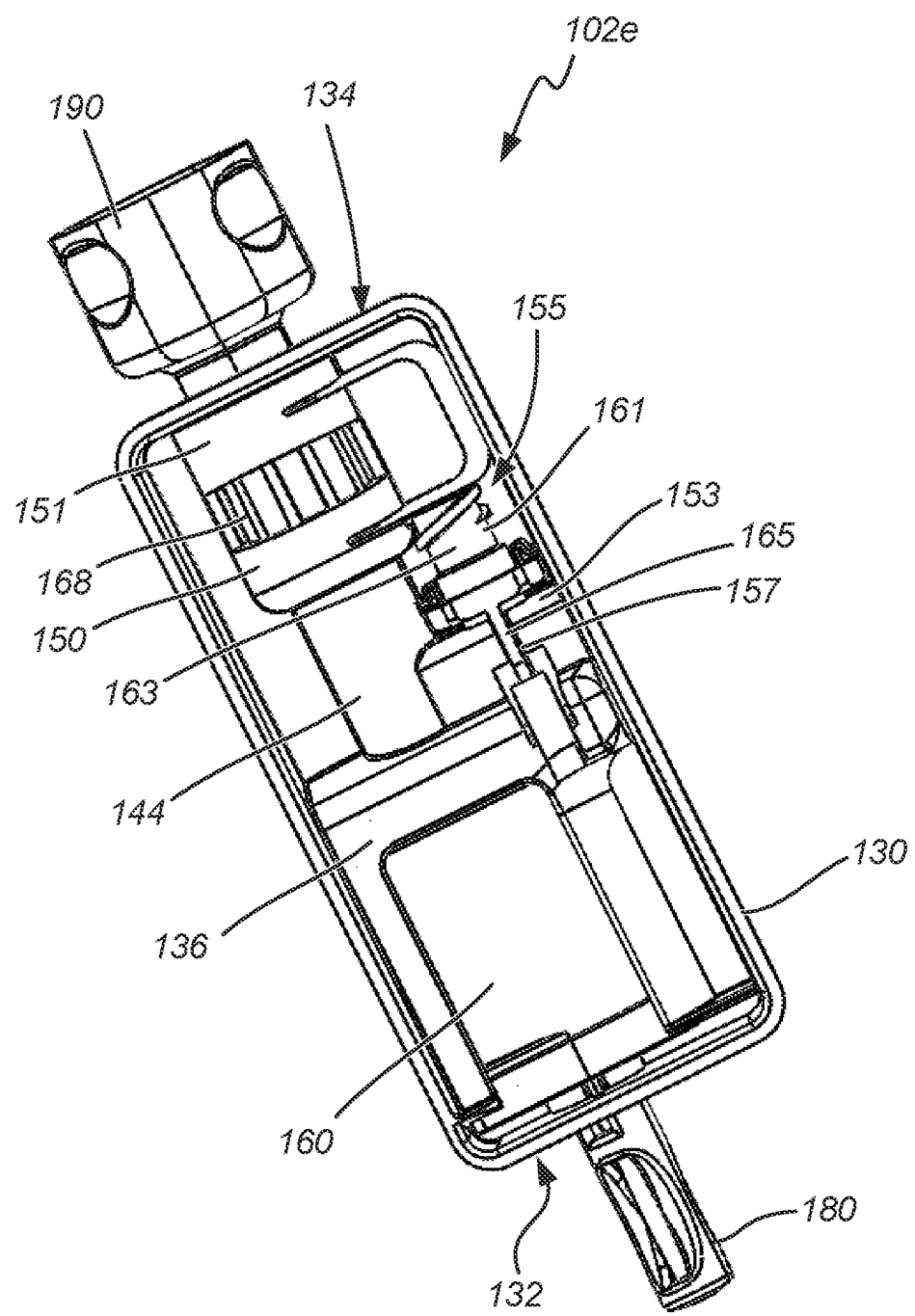
Figure 20B:
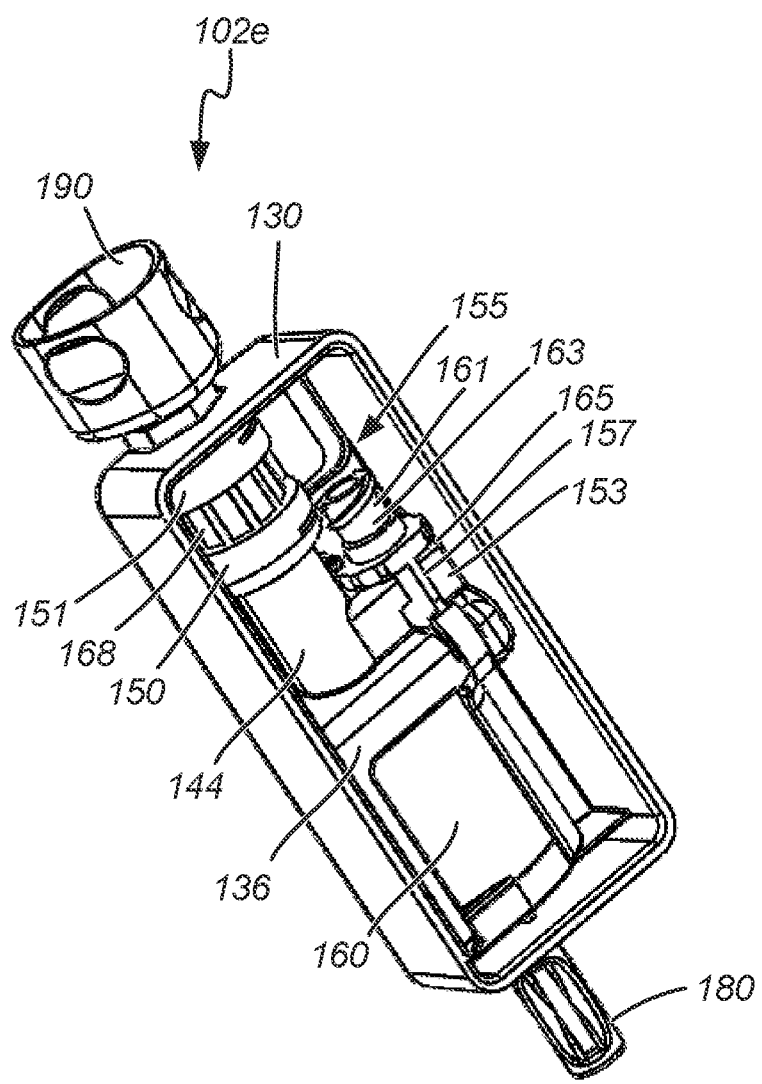
Figure 20C:
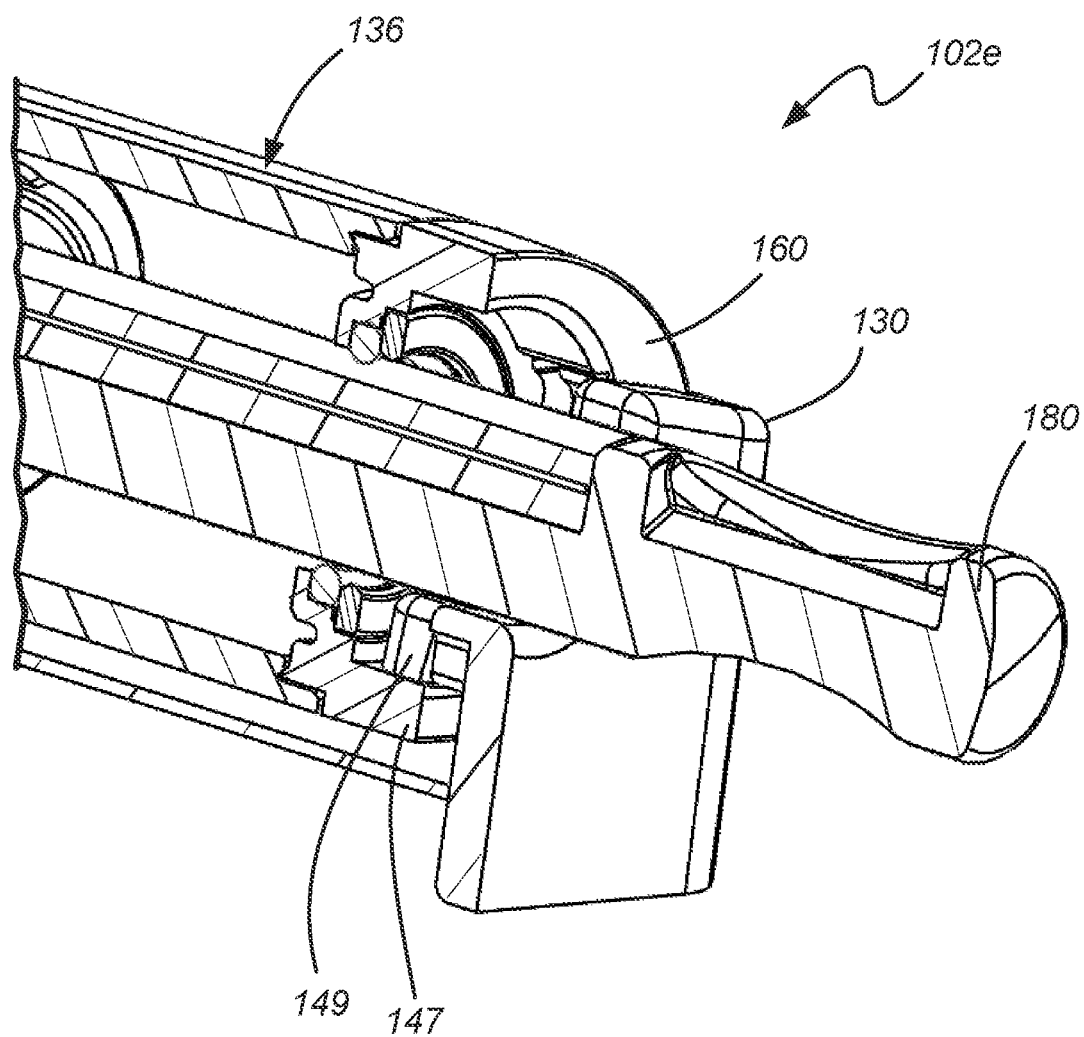
FIG. 20C is a partial cross-sectional view of a portion of the cartridge and/or vial supporter of FIGS. 19A-19B and 20A-20B.

Still referring to FIGS. 19A-20B, cartridge 160 further includes a fitting cap 161. In some embodiments, plug 165 of fitting cap 161 can be inserted onto cartridge fitting 168 by pressing or rotating cap 163 of fitting cap 161 after the cartridge has been filled with medicament and removed from supporter 102e to seal the cartridge to prevent leakage of medicament if the cartridge is going to be stored and not immediately connected to a pump. Supporter 102e also provides a fitting cap holder 153 that includes a recess 155 into which cap 163 of fitting cap 161 fits and a slot 157 into which plug 165 of fitting cap 161 is received. A portion of plug 165, as shown in FIG. 19, extends through supporter 102e such that fitting cap 161 can be removed from supporter 102e by a user pushing down on plug 165 from that side. In prior art systems that utilize a similar fitting cap, the cap is generally provided loosely in the system packaging and, as such, can easily fall out and become lost, contaminated, etc. upon opening the packaging. One advantage of having a fitting cap holder 153 in the tray body 130 in embodiments of the present invention is that when the device is initially removed from the packaging, the fitting cap 161 is secured to the tray body and can therefore be both easily located for use and prevented from falling out.

Figure 18A:
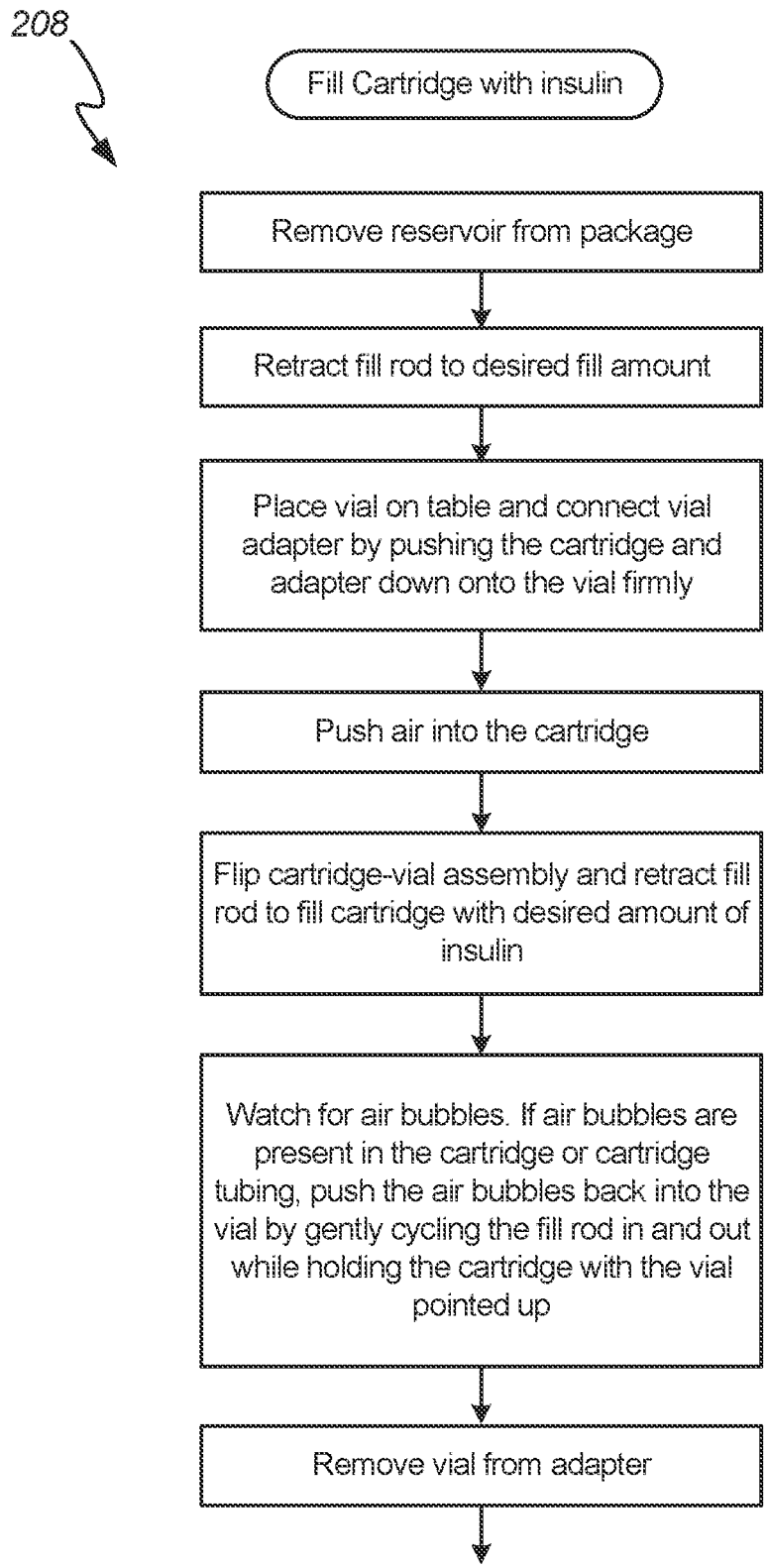
FIGS. 18A-18B are a flowchart depicting a method of filling a cartridge using a vial supporter, according to an embodiment of the invention.
Figure 18B:
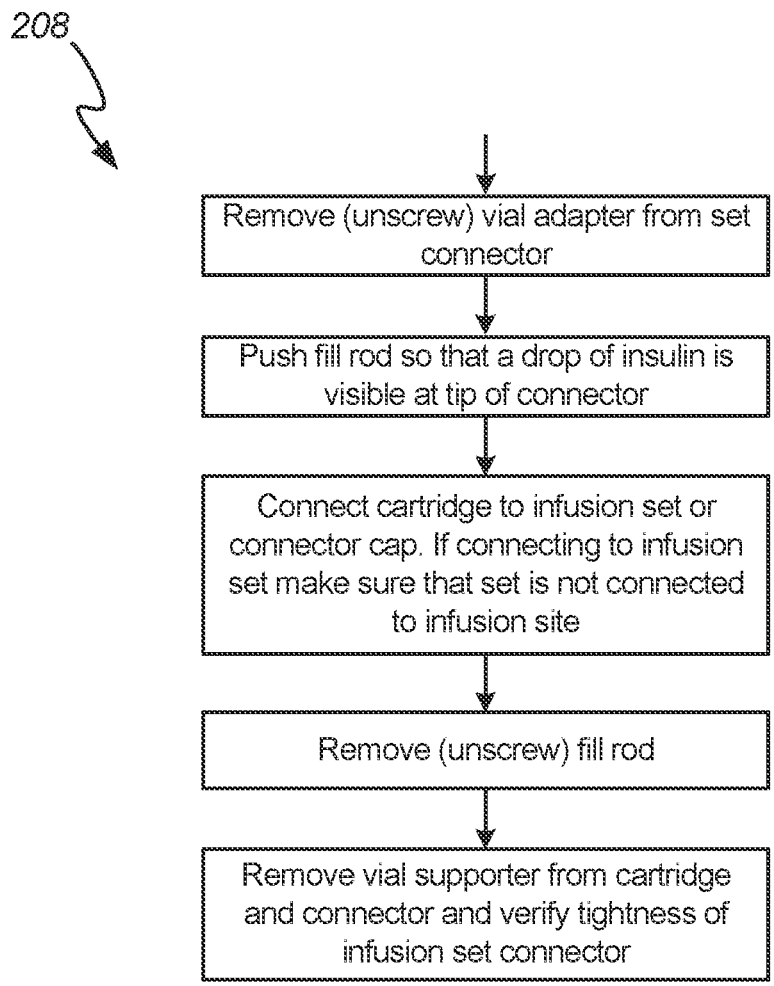

Referring now to FIGS. 18A and 18B, a method 208 for filling a medicament cartridge of an ambulatory, user-wearable infusion pump according to an embodiment of the invention is depicted and described. Generally, the method includes coupling the cartridge to a vial supporter and to a vial. Example vial supporters suitable for use with such a method are depicted in FIGS. 1-4 and 6-7. With the fill rod retracted, air is pushed into the cartridge. The components are then arranged such that the vial is the highest point, and the fill rod is retracted to draw medicament from the vial into the cartridge. The vial can be removed from the adapter, and the adapted removed from the interconnect fitting of the cartridge. The cartridge can then be attached to an infusion set, and the fill rod and vial supporter are uncoupled from the cartridge and placed aside until the cartridge needs to be filled again.

Figure 21:
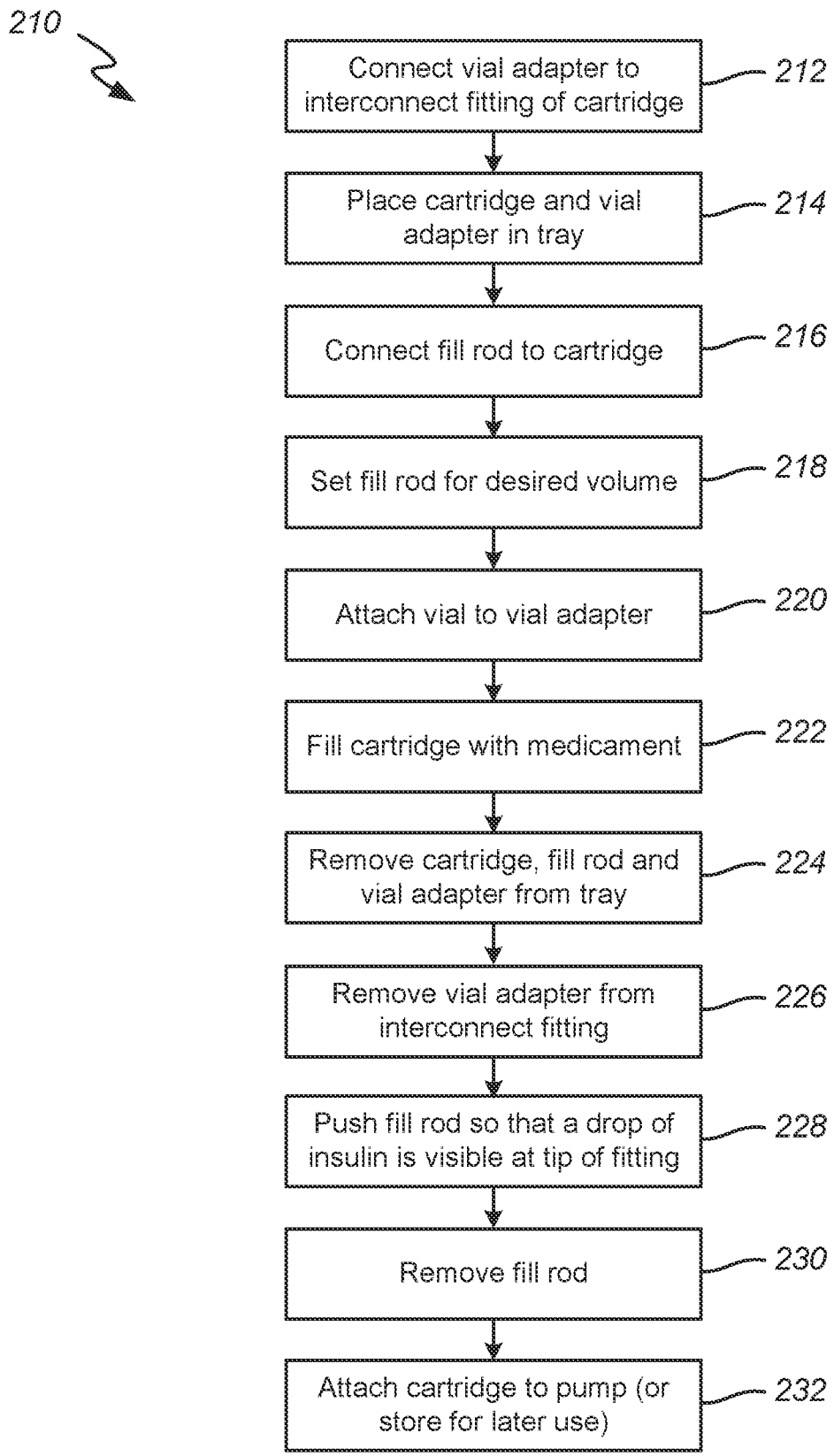
FIG. 21 is a flowchart depicting a method of filling a cartridge using a cartridge and/or vial supporter according to an embodiment of the present invention.

Referring now to FIG. 21, a method 210 for filling a medicament cartridge of an ambulatory, user-wearable infusion pump according to another embodiment is depicted and described. Example cartridge and/or vial supporters suitable for use with the depicted method include, for example, the cartridge and/or vial supporters shown in FIGS. 8-11, 12-14 and 19A-20C. Method 210 includes connecting a vial adapter to an interconnect fitting of a medicament cartridge at step 212, such as shown in, for example, FIG. 13. The cartridge, including a tubing portion extending from cartridge and the interconnect fitting, and connected vial adapter can then be seated in a supporter configured as a tray at step 214 as described above. The tray can include recessed holders defined therein that are sized and shaped to receive the cartridge, tubing portion and interconnect fitting. In some embodiments, the tray also includes a vial adapter holder that retains a portion of the vial adapter. In some embodiments, one or more of a portion of cartridge and a portion of interconnect fitting can create a snap fit with one or more tabs on tray to aid in retaining those components in the tray. A fill rod can then be inserted through a portion of the tray and connected to the cartridge at step 216, although in the embodiment depicted in FIGS. 19A-19B and 20A-20C the fill rod can be inserted either prior to or after seating the cartridge in the cartridge holder. Such a seated configuration is shown in, for example, FIGS. 8-12 and 19-20. In some embodiments, the system may come pre-packaged in this configuration before initial use of the cartridge. When the cartridge is refilled, steps 212-216 must be repeated.

Once the cartridge is in the above-described filling configuration in the tray, at step 218 the fill rod can be positioned to set a desired fill volume. A vial containing the medicament that is to be infused into the cartridge can then be attached to the vial adapter at step 220, though it should be noted that the vial could alternatively be connected to the vial adapter at any earlier portion of the method. The cartridge can then be filled with the desired volume of the medicament at step 222 and the vial removed. As further described and depicted in FIGS. 18A-18B, filling the cartridge can include depressing the fill rod to push air into the cartridge, then retracting the fill rod to fill the cartridge with the desired amount, and then checking for air bubbles in the cartridge before removing the vial. In some embodiments, the cartridge can comprise a clear material in the reservoir area where the medicament is contained and the tray can include a rear opening, such as opening 140 described above, to aid in inspecting the cartridge for air bubbles as well as observing the volume of medicament in the cartridge. The cartridge, fill rod and vial adapter can be removed from the tray at step 224. In some embodiments, the cartridge removal can be aided by one or more tabs that release portions of the system that were snap fit into the tray as described above. In embodiments employing a rear opening for visual inspection of the cartridge, this opening can further aid in cartridge removal by providing easy access for the user to press on the cartridge to push it out of the tray. It should be noted that in embodiments such as those depicted in FIGS. 8-14 in which ring 142 cooperates with fill rod 180 to retain the cartridge in tray 130, fill rod 180 must first be removed prior to removing the cartridge and vial adapter. Following removal of the cartridge from the tray, the vial adapter can be disconnected from the interconnect fitting at step 226.

The cartridge is now filled and is readied for use by pushing the fill rod so that a drop of medicament such as insulin is visible at the top of the interconnect fitting and an infusion set attached to interconnect fitting at step 228. The fill rod can then be removed at step 230. The cartridge can now be attached to a user-wearable, ambulatory infusion pump at step 232. Alternatively, if the cartridge is not going to be stored rather than immediately attached to a pump, a fitting cap such as fitting cap 161 can be inserted into interconnect fitting of cartridge rather than attaching the fitting to an infusion set to preclude accidental leakage of fluid from cartridge.

Figure 22:
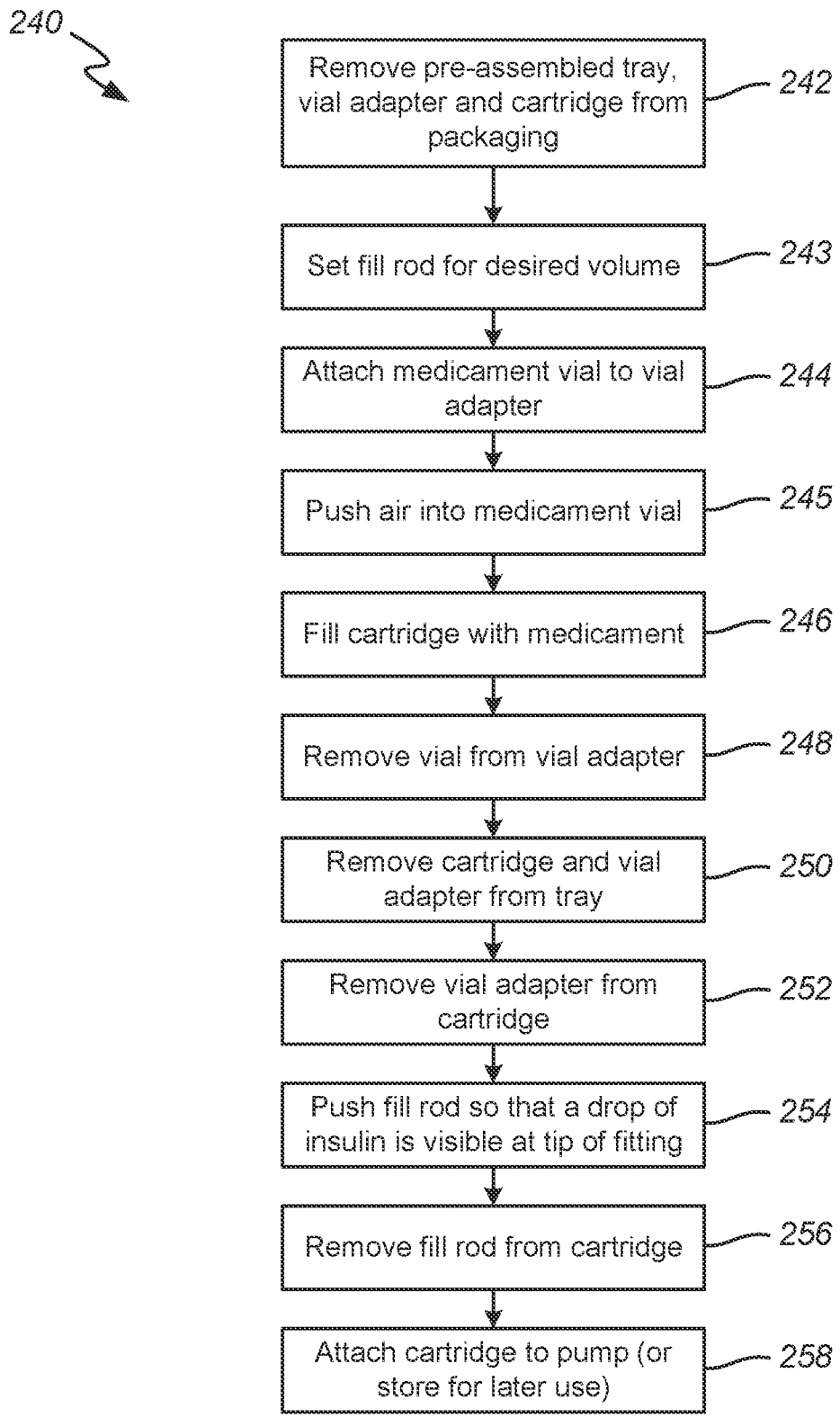
FIG. 22 is a flowchart depicting a method of filling a cartridge using a cartridge and/or vial supporter according to an embodiment of the present invention.

Referring now to FIG. 22, a method 240 for filling a medicament cartridge of an ambulatory, user-wearable infusion pump according to another embodiment is depicted and described. The depicted method is suitable for use with, for example, the cartridge and/or vial supporters shown in FIGS. 8-11, 12-14 and 19A-20C. In this embodiment, tray body 130, vial adapter 190 and cartridge 160 (and fill rod 180) are provided to the user pre-assembled. At step 242, the user removes this pre-assembled combination from the product packaging, sets the desired fill volume with the fill rod at step 243 and connects a medicament vial to the vial adapter at step 244. After pushing air into the medicament vial with the fill rod at step 245, the cartridge is then filled with medicament at step 246 as described above and the vial removed from the vial adapter at step 248. The cartridge and vial adapter can then be removed from the tray at step 250 followed by removal of the vial adapter from the cartridge at step 252. The fill rod is then pushed so that a drop of medicament such as insulin is visible at the tip of the fitting at step 254 and the fill rod removed from the cartridge at step 256 as described above. The filled cartridge can now be attached to the pump or stored for later use at step 258.

Figure 23:
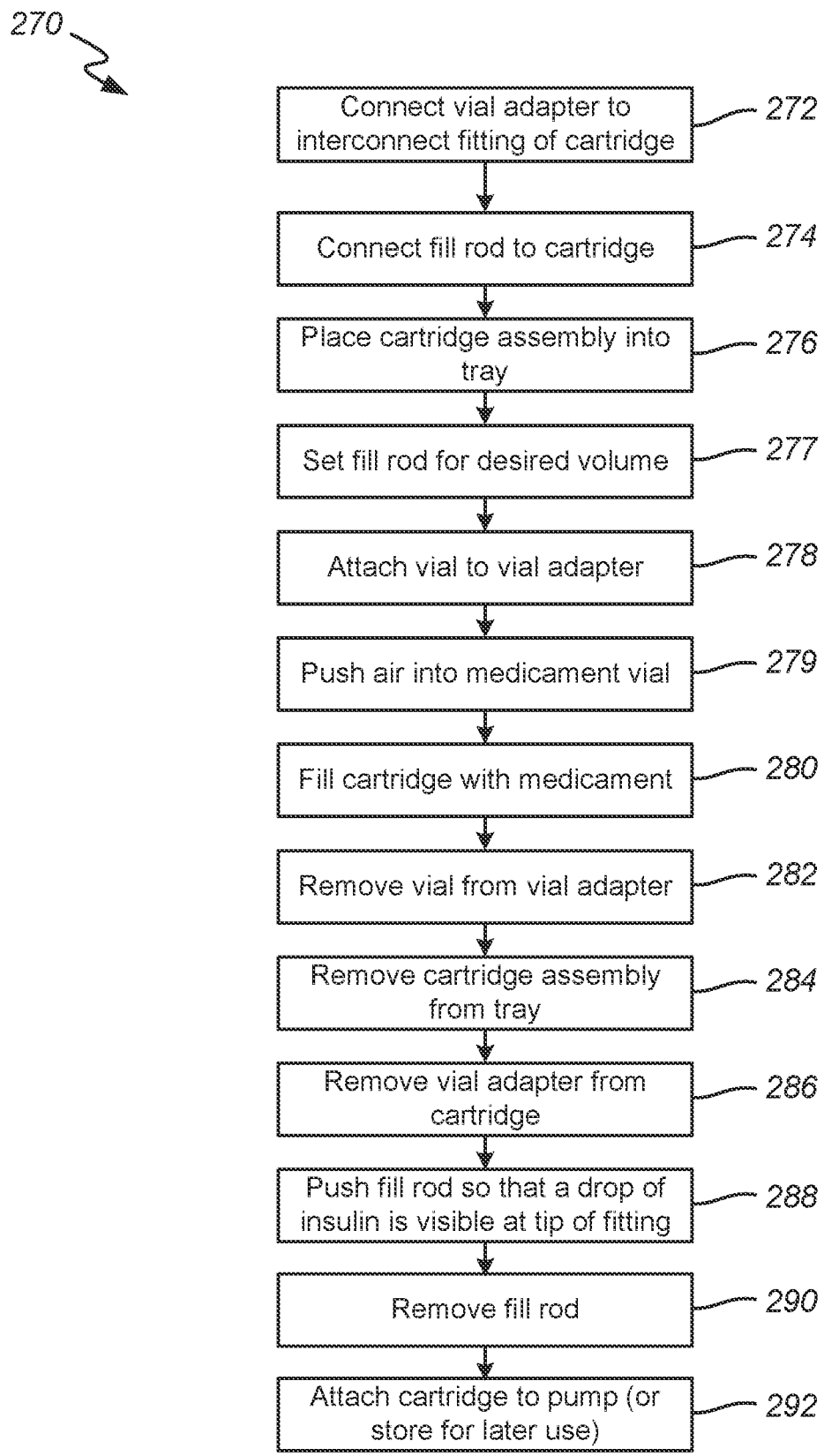
FIG. 23 is a flowchart depicting a method of filling a cartridge using a cartridge and/or vial supporter according to an embodiment of the present invention.

FIG. 23 depicts another method 270 for filling a medicament cartridge of an ambulatory, user-wearable infusion pump according to an embodiment of the infusion with a cartridge and/or vial supporter configured as a tray. Unlike the method 240 described with respect to FIG. 22 in which components of the system are provided to the user pre-assembled, in this embodiment the user must assemble the cartridge components for filling. Such a procedure may occur when a user is refilling a cartridge after one or more initial uses. At step 272 the vial adapter is connected to the interconnect fitting of the cartridge and at step 274 the fill rod is connected to the cartridge. This assembly can then be placed into the cartridge tray at step 276. The fill rod can be set for a desired fill volume at step 277 and the medicament vial can be connected to the vial adapter at step 278. Air can be pushed into the medicament vial with the fill rod at step 279 and the cartridge filled with medicament at step 280. The medicament vial is then removed from the vial adapter at step 282 and the cartridge assembly removed from the tray at step 284. The filled cartridge can then be readied for use as described previously by removing the vial adapter from the interconnect fitting at step 286, pushing the fill rod so that a drop of medicament such as insulin is visible at the tip of the fitting at step 288 and removing the fill rod at step 290. The filled cartridge is now ready to be attached to a pump (and infusion set) or stored for later use, as described herein, at step 292.

Also incorporated herein by reference in their entirety are commonly owned U.S. Pat. Nos. 8,287,495; 8,408,421 8,448,824; 8,573,027; 8,650,937; 8,986,523; 9,173,998; 9,180,242; 9,180,243; 9,238,100; 9,242,043; 9,335,910; 9,381,271; 9,421,329; 9,486,171; 9,486,571; 9,492,608; 9,503,526; 9,555,186; 9,565,718; 9,603,995; 9,669,160; 9,715,327; 9,737,656; and 9,750,871 commonly owned U.S. Patent Publication Nos. 2009/0287180; 2012/0123230; 2013/0053816; 2014/0276419; 2014/0276420; 2014/0276423; 2014/0276531; 2014/0276556 2014/0276569; 2014/0276570; 2014/0378898; 2015/0073337; 2015/0182693; 2016/0082188; 2016/0339172; 2017/0049957; 2017/0142658; 2017/0182248; and 2017/0250971 and commonly owned U.S. patent application Ser. Nos. 14/707,851 and 15/564,895 and commonly owned U.S. Provisional Application Ser. Nos. 61/911,576; 61/920,902; 61/920,914; 61/920,940; 62/139,275; 62/352,164; 62/445,041; and 62/545,228.

Further incorporated by reference herein in their entirety are U.S. Pat. Nos. 8,601,465; 8,502,662; 8,452,953; 8,451,230; 8,449,523; 8,444,595; 8,343,092; 8,285,328; 8,126,728; 8,117,481; 8,095,123; 7,999,674; 7,819,843; 7,782,192; 7,109,878; 6,997,920; 6,979,326; 6,936,029; 6,872,200; 6,813,519; 6,641,533; 6,554,798; 6,551,276; 6,295,506; and 5,665,065.

Various embodiments of systems, devices, and methods have been described herein. These embodiments are given only by way of example and are not intended to limit the scope of the claimed inventions. It should be appreciated, moreover, that the various features of the embodiments that have been described may be combined in various ways to produce numerous additional embodiments. Moreover, while various materials, dimensions, shapes, configurations and locations, etc. have been described for use with disclosed embodiments, others besides those disclosed may be utilized without exceeding the scope of the claimed inventions.

Persons of ordinary skill in the relevant arts will recognize that the subject matter hereof may comprise fewer features than illustrated in any individual embodiment described above. The embodiments described herein are not meant to be an exhaustive presentation of the ways in which the various features of the subject matter hereof may be combined. Accordingly, the embodiments are not mutually exclusive combinations of features; rather, the various embodiments can comprise a combination of different individual features selected from different individual embodiments, as understood by persons of ordinary skill in the art. Moreover, elements described with respect to one embodiment can be implemented in other embodiments even when not described in such embodiments unless otherwise noted.

Although a dependent claim may refer in the claims to a specific combination with one or more other claims, other embodiments can also include a combination of the dependent claim with the subject matter of each other dependent claim or a combination of one or more features with other dependent or independent claims. Such combinations are proposed herein unless it is stated that a specific combination is not intended.

Any incorporation by reference of documents above is limited such that no subject matter is incorporated that is contrary to the explicit disclosure herein. Any incorporation by reference of documents above is further limited such that no claims included in the documents are incorporated by reference herein. Any incorporation by reference of documents above is yet further limited such that any definitions provided in the documents are not incorporated by reference herein unless expressly included herein.

For purposes of interpreting the claims, it is expressly intended that the provisions of 35 U.S.C. § 112(f) are not to be invoked unless the specific terms "means for" or "step for" are recited in a claim.

The invention claimed is:

1. A device for supporting a medicament cartridge of an ambulatory infusion pump during a procedure for filling the medicament cartridge with a medicament, comprising:
    a monolithic tray body having a cartridge end and a vial end;
    a cartridge holder defined adjacent the cartridge end in the tray body, the cartridge holder comprising a cartridge recess in the tray body, the cartridge recess having a bottom surface and a perimeter shape generally matching an outer perimeter of a body of the medicament cartridge configured to be retained in the cartridge holder;
    a fitting holder defined in the tray body, the fitting holder comprising a fitting recess in the tray body that is configured to retain an interconnect fitting of the medicament cartridge and having a fitting recess shape generally matching a shape of the interconnect fitting; and
    a vial adapter holder defined in the tray body adjacent the fitting holder at the vial end of the tray body, the vial adapter holder comprising a vial adapter recess in the tray body that is configured to retain a portion of a vial adapter configured to attach to the interconnect fitting of the medicament cartridge to facilitate filling of the medicament cartridge with a vial of medicament attached to the vial adapter,
    wherein the vial adapter recess is configured to prevent rotation of the vial adapter about a longitudinal axis of the of the vial adapter recess when disposed within the vial adapter recess to prevent the vial adapter from being disconnected from the interconnect fitting.

2. The device of claim 1, wherein the vial adapter recess is disposed at an edge of the cartridge end of the tray body such that the portion of the vial adapter retained in the vial adapter recess is disposed in the tray body and another portion of the vial adapter protrudes longitudinally outwardly from the tray body.

3. The device of claim 1, wherein the vial adapter recess has a partial hexagonal configuration configured to retain a hexagonal portion of the vial adapter.

4. The device of claim 1, wherein the fitting holder and the vial adapter holder are formed as one continuous recess in the tray body.

5. The device of claim 4, wherein the cartridge holder, the fitting holder and the vial adapter holder are formed as one continuous recess in the tray body.

6. The device of claim 1, further comprising a tubing holder defined in the tray body, the tubing holder comprising a channel disposed between the cartridge holder and the fitting holder configured to retain a tubing section of the medicament cartridge.

7. The device of claim 1, further comprising an opening in the bottom surface of the recess of the cartridge holder through which a portion of the medicament cartridge is visible when the medicament cartridge is disposed in the cartridge holder.

8. A system for filling a medicament cartridge of an ambulatory infusion pump with a medicament, comprising:
    a medicament cartridge having a cartridge body defining an outer perimeter, a tubing section extending from the cartridge body and an interconnect fitting at a distal end of the tubing section; and
    a cartridge supporter configured to support and retain the medicament cartridge during a procedure for filling the medicament cartridge with the medicament without covering the medicament cartridge, the cartridge supporter defining a monolithic tray body having a cartridge end and a vial end and including a cartridge holder recess having a perimeter shape generally matching the outer perimeter of the cartridge body, a fitting holder recess having a shape generally matching a shape of the interconnect fitting and a vial adapter recess; and
    a vial adapter configured to attach to the interconnect fitting to facilitate filling of the medicament cartridge with a vial of medicament attached to the vial adapter, wherein the vial adapter recess is configured to prevent rotation of the vial adapter about a longitudinal axis of the of the vial adapter recess when disposed within the vial adapter recess to prevent the vial adapter from being disconnected from the interconnect fitting.

9. The system of claim 8, wherein the vial adapter recess is disposed at an edge of the cartridge end of the tray body such that the portion of the vial adapter retained in the vial adapter recess is disposed in the tray body and another portion of the vial adapter protrudes longitudinally outwardly from the tray body.

10. The system of claim 8, wherein the vial adapter recess has a partial hexagonal configuration configured to retain a hexagonal portion of the vial adapter.

11. The system of claim 8, wherein the fitting holder recess and the vial adapter recess are formed as one continuous recess in the tray body.

12. The system of claim 11, wherein the cartridge holder recess, wherein the fitting holder recess and the vial adapter recess are formed as one continuous recess in the tray body.

13. The system of claim 8, further comprising a tubing holder recess defined in the tray body, the tubing holder recess comprising a channel disposed between the cartridge holder recess and the fitting holder recess configured to retain the tubing section of the medicament cartridge.

14. The system of claim 8, further comprising an opening in the bottom surface of the cartridge holder recess through which a portion of the medicament cartridge is visible when the medicament cartridge is disposed in the cartridge holder recess.

15. The system of claim 8, further comprising a medicament vial configured to couple with the vial adapter opposite of the interconnect fitting.

16. The system of claim 8, further comprising a pump configured to couple with the medicament cartridge to deliver medicament from the medicament cartridge to the user.

17. The system of claim 8, wherein the medicament cartridge comprises a clear material around at least a portion of an area of the medicament cartridge configured to contain the medicament that enables visual inspection of the medicament.

18. The system of claim 17, wherein the clear material of the medicament cartridge includes graduated markings delineating volume levels of the medicament in the medicament cartridge.

* * * * *